(12) United States Patent
Kubiak

(10) Patent No.: US 9,381,019 B2
(45) Date of Patent: Jul. 5, 2016

(54) SYSTEM FOR TISSUE FIXATION TO BONE

(71) Applicant: University of Utah Research Foundation, Salt Lake City, UT (US)

(72) Inventor: Erik N. Kubiak, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 0 days.

(21) Appl. No.: 14/461,378

(22) Filed: Aug. 16, 2014

(65) Prior Publication Data

US 2015/0039000 A1    Feb. 5, 2015

Related U.S. Application Data

(62) Division of application No. 13/021,651, filed on Feb. 4, 2011, now Pat. No. 8,852,214.

(51) Int. Cl.
- *A61B 17/11* (2006.01)
- *A61F 2/08* (2006.01)
- *A61B 17/00* (2006.01)

(52) U.S. Cl.
CPC .......... *A61B 17/1146* (2013.01); *A61F 2/0811* (2013.01); *A61B 2017/00004* (2013.01)

(58) Field of Classification Search
CPC ............ A61B 17/1146; A61B 17/8085; A61F 2/0811; A61F 2002/0817–2002/0894; A61F 2002/30378; A61F 2/0059; A61F 2/0063
See application file for complete search history.

(56) References Cited

U.S. PATENT DOCUMENTS

| | | | |
|---|---|---|---|
| 3,166,072 A | 1/1965 | Sullivan et al. | |
| 4,388,926 A | 6/1983 | Shalaby et al. | |
| 4,414,967 A | 11/1983 | Shapiro | |
| 4,461,298 A | 7/1984 | Shalaby et al. | |
| 4,469,101 A | 9/1984 | Coleman et al. | |
| 4,489,875 A | 12/1984 | Crawford et al. | |
| 4,548,202 A | 10/1985 | Duncan | |
| 4,610,250 A | 9/1986 | Green | |
| 4,655,980 A | 4/1987 | Chu | |
| 4,776,890 A | 10/1988 | Chu | |
| 4,810,549 A | 3/1989 | Abrams et al. | |
| 4,873,976 A | 10/1989 | Schreiber | |
| 4,942,875 A | 7/1990 | Hlavacek et al. | |

(Continued)

OTHER PUBLICATIONS

McKenzie, "An Experimental Multiple Barbed Suture for the Long Flexor Tendons of the Palm and Fingers," Journal of Bone and Joint Surgery, Aug. 1967, pp. 440-447, vol. 49 B, No. 3.

Momose et al., "Suture Techniques With High Breaking Strength and Low Gliding Resistance: Experiments in the Dog Flexor Digitorum Pofundus Tendon," Acta Orthop Scand, 2001, 72(6):635-641.

(Continued)

*Primary Examiner* — Julian W Woo
*Assistant Examiner* — Shaun L David
(74) *Attorney, Agent, or Firm* — David L. Stott

(57) ABSTRACT

Methods and systems are provided for fixating connective tissue to bone. Some aspects include a carrier member having a length, width, and thickness, wherein the length and width are each at least two times greater than the thickness; attachment members extending from the carrier member and that engage connective tissue of an animal; and a bone engaging member extending from the carrier member and configured to attach to a bone of the animal. In some aspects, when the attachment members are engaged with the connective tissue and the bone engaging member is attached to the bone, the connective tissue and the bone are limited in being pulled apart from one another during physiological use of the connective tissue.

20 Claims, 27 Drawing Sheets

(56) References Cited

U.S. PATENT DOCUMENTS

| | | |
|---|---|---|
| 4,946,467 A | 8/1990 | Ohi et al. |
| 4,960,420 A | 10/1990 | Goble et al. |
| 4,983,184 A | 1/1991 | Steinemann |
| 5,047,103 A | 9/1991 | Abrams et al. |
| 5,061,283 A | 10/1991 | Silvestrini |
| 5,163,956 A | 11/1992 | Liu et al. |
| 5,207,851 A | 5/1993 | Abrams |
| 5,250,049 A | 10/1993 | Michael |
| 5,290,552 A | 3/1994 | Sierra et al. |
| 5,292,334 A | 3/1994 | Howansky |
| 5,306,500 A | 4/1994 | Rhee et al. |
| 5,312,023 A | 5/1994 | Green et al. |
| 5,326,013 A | 7/1994 | Green et al. |
| 5,329,943 A | 7/1994 | Johnson |
| 5,342,376 A | 8/1994 | Ruff |
| 5,346,746 A | 9/1994 | Abrams |
| 5,413,791 A | 5/1995 | Rhee et al. |
| 5,446,091 A | 8/1995 | Rhee et al. |
| 5,447,265 A | 9/1995 | Vidal et al. |
| 5,458,636 A | 10/1995 | Brancato |
| 5,465,894 A | 11/1995 | Clark et al. |
| 5,480,644 A | 1/1996 | Freed |
| 5,510,418 A | 4/1996 | Rhee et al. |
| 5,523,348 A | 6/1996 | Rhee et al. |
| 5,527,341 A | 6/1996 | Gogolewski et al. |
| 5,542,594 A | 8/1996 | McKean et al. |
| 5,575,803 A | 11/1996 | Cooper et al. |
| 5,580,923 A | 12/1996 | Yeung et al. |
| 5,597,637 A | 1/1997 | Abrams et al. |
| 5,603,443 A | 2/1997 | Clark et al. |
| 5,607,094 A | 3/1997 | Clark et al. |
| 5,630,842 A | 5/1997 | Brodniewicz |
| 5,667,839 A | 9/1997 | Berg |
| 5,711,472 A | 1/1998 | Bryan |
| 5,716,981 A | 2/1998 | Hunter et al. |
| 5,723,008 A | 3/1998 | Gordon |
| 5,728,110 A | 3/1998 | Vidal et al. |
| 5,732,871 A | 3/1998 | Clark et al. |
| 5,756,678 A | 5/1998 | Shenoy et al. |
| 5,766,250 A * | 6/1998 | Chervitz ............ A61B 17/1675 606/232 |
| 5,800,544 A | 9/1998 | Demopulos et al. |
| 5,807,581 A | 9/1998 | Rosenblatt et al. |
| 5,858,156 A | 1/1999 | Abrams et al. |
| 5,860,229 A | 1/1999 | Morgenstern |
| 5,865,361 A | 2/1999 | Milliman et al. |
| 5,908,427 A | 6/1999 | McKean et al. |
| 5,916,224 A | 6/1999 | Esplin |
| 5,961,520 A | 10/1999 | Beck, Jr. et al. |
| 5,964,774 A | 10/1999 | McKean et al. |
| 5,980,524 A | 11/1999 | Justin et al. |
| 5,997,811 A | 12/1999 | Esposito |
| 6,010,764 A | 1/2000 | Abrams |
| 6,030,410 A | 2/2000 | Zurbrugg |
| 6,045,560 A | 4/2000 | McKean et al. |
| 6,079,606 A | 6/2000 | Milliman et al. |
| 6,080,192 A | 6/2000 | Demopulos et al. |
| 6,083,332 A | 7/2000 | Abrams |
| 6,086,547 A | 7/2000 | Hanssen et al. |
| 6,099,538 A | 8/2000 | Moses et al. |
| 6,106,556 A | 8/2000 | Demopulos et al. |
| 6,110,560 A | 8/2000 | Abrams |
| 6,111,165 A | 8/2000 | Berg |
| 6,241,139 B1 | 6/2001 | Milliman et al. |
| 6,241,747 B1 | 6/2001 | Ruff |
| 6,277,394 B1 | 8/2001 | Sierra |
| 6,330,965 B1 | 12/2001 | Milliman et al. |
| 6,333,347 B1 | 12/2001 | Hunter et al. |
| 6,358,557 B1 | 3/2002 | Wang et al. |
| 6,383,199 B2 | 5/2002 | Carter et al. |
| 6,413,742 B1 | 7/2002 | Olsen et al. |
| D462,766 S | 9/2002 | Jacobs et al. |
| 6,472,171 B1 | 10/2002 | Toman et al. |
| 6,485,503 B2 | 11/2002 | Jacobs et al. |
| 6,495,127 B1 | 12/2002 | Wallace et al. |
| 6,515,016 B2 | 2/2003 | Hunter |
| 6,551,315 B2 | 4/2003 | Kortenbach et al. |
| 6,644,532 B2 | 11/2003 | Green et al. |
| 6,645,226 B1 | 11/2003 | Jacobs et al. |
| 6,669,073 B2 | 12/2003 | Milliman et al. |
| 6,689,803 B2 | 2/2004 | Hunter |
| 6,712,830 B2 | 3/2004 | Esplin |
| 6,716,226 B2 | 4/2004 | Sixto, Jr. et al. |
| 6,740,100 B2 | 5/2004 | Demopulos et al. |
| 6,743,240 B2 | 6/2004 | Smith et al. |
| 6,773,450 B2 | 8/2004 | Leung et al. |
| 6,824,548 B2 | 11/2004 | Smith et al. |
| 6,830,174 B2 | 12/2004 | Hillstead et al. |
| 6,843,794 B2 | 1/2005 | Sixto, Jr. et al. |
| 6,877,647 B2 | 4/2005 | Green et al. |
| 6,893,452 B2 | 5/2005 | Jacobs |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,962,594 B1 | 11/2005 | Thevenet |
| 6,991,643 B2 | 1/2006 | Saadat |
| 7,016,194 B1 | 3/2006 | Wong |
| 7,056,331 B2 | 6/2006 | Kaplan et al. |
| 7,070,602 B2 | 7/2006 | Smith et al. |
| 7,090,685 B2 | 8/2006 | Kortenbach et al. |
| 7,121,446 B2 | 10/2006 | Arad et al. |
| 7,129,209 B2 | 10/2006 | Rhee |
| 7,156,862 B2 | 1/2007 | Jacobs et al. |
| 7,172,615 B2 | 2/2007 | Morriss et al. |
| 7,176,256 B2 | 2/2007 | Rhee et al. |
| 7,226,468 B2 | 6/2007 | Ruff |
| 7,229,413 B2 | 6/2007 | Violante et al. |
| 7,232,445 B2 | 6/2007 | Kortenbach et al. |
| 7,296,724 B2 | 11/2007 | Green et al. |
| 7,303,107 B2 | 12/2007 | Milliman et al. |
| 7,309,346 B2 | 12/2007 | Martinek |
| 7,328,829 B2 | 2/2008 | Arad et al. |
| 7,343,920 B2 | 3/2008 | Toby et al. |
| 7,354,627 B2 | 4/2008 | Pedrozo et al. |
| 7,398,907 B2 | 7/2008 | Racenet et al. |
| 7,401,720 B1 | 7/2008 | Durrani |
| 7,438,209 B1 | 10/2008 | Hess et al. |
| 7,464,848 B2 | 12/2008 | Green et al. |
| 7,510,566 B2 | 3/2009 | Jacobs et al. |
| 7,530,484 B1 | 5/2009 | Durrani |
| 7,565,993 B2 | 7/2009 | Milliman et al. |
| 7,568,604 B2 | 8/2009 | Ehrenfels et al. |
| 7,600,663 B2 | 10/2009 | Green |
| 7,604,151 B2 | 10/2009 | Hess et al. |
| 7,611,038 B2 | 11/2009 | Racenet et al. |
| 7,611,521 B2 | 11/2009 | Lubbers et al. |
| 7,615,058 B2 | 11/2009 | Sixto, Jr. et al. |
| 7,624,487 B2 | 12/2009 | Trull et al. |
| 7,635,074 B2 | 12/2009 | Olson et al. |
| 7,641,091 B2 | 1/2010 | Olson et al. |
| 7,665,646 B2 | 2/2010 | Prommersberger |
| 7,708,759 B2 | 5/2010 | Lubbers et al. |
| 7,727,246 B2 | 6/2010 | Sixto, Jr. et al. |
| 7,727,248 B2 | 6/2010 | Smith et al. |
| 7,771,468 B2 | 8/2010 | Whitbourne et al. |
| 7,819,896 B2 | 10/2010 | Racenet |
| 7,824,426 B2 | 11/2010 | Racenet et al. |
| 7,828,189 B2 | 11/2010 | Holsten et al. |
| 7,842,097 B2 | 11/2010 | Yamamoto et al. |
| 7,845,533 B2 | 12/2010 | Marczyk et al. |
| 7,861,907 B2 | 1/2011 | Green et al. |
| 7,891,531 B1 | 2/2011 | Ward |
| 7,909,224 B2 | 3/2011 | Prommersberger |
| 7,926,692 B2 | 4/2011 | Racenet et al. |
| 7,942,304 B2 | 5/2011 | Taylor et al. |
| 7,942,885 B2 | 5/2011 | Sixto, Jr. et al. |
| 7,950,561 B2 | 5/2011 | Aranyi |
| 8,006,700 B2 | 8/2011 | Demopulos et al. |
| 8,008,598 B2 | 8/2011 | Whitman et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,021,378 B2 | 9/2011 | Sixto, Jr. et al. |
| 8,029,563 B2 | 10/2011 | House et al. |

(56) References Cited

U.S. PATENT DOCUMENTS

| | | | |
|---|---|---|---|
| 8,033,439 B2 | 10/2011 | Racenet et al. |
| 8,038,045 B2 | 10/2011 | Bettuchi et al. |
| 8,043,328 B2 | 10/2011 | Hahnen et al. |
| 8,062,314 B2 | 11/2011 | Sixto, Jr. et al. |
| 8,062,330 B2 | 11/2011 | Prommersberger et al. |
| 8,062,363 B2 | 11/2011 | Hirpara et al. |
| 8,066,721 B2 | 11/2011 | Kortenbach et al. |
| 8,070,033 B2 | 12/2011 | Milliman et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,113,409 B2 | 2/2012 | Cohen et al. |
| 8,114,129 B2 | 2/2012 | Lubbers et al. |
| 8,118,834 B1 | 2/2012 | Goraltchouk et al. |
| 8,123,101 B2 | 2/2012 | Racenet et al. |
| 8,141,762 B2 | 3/2012 | Bedi et al. |
| 8,157,151 B2 | 4/2012 | Ingmanson et al. |
| 8,186,557 B2 | 5/2012 | Cohen et al. |
| 8,186,560 B2 | 5/2012 | Hess et al. |
| 8,205,620 B2 | 6/2012 | Taylor et al. |
| 8,210,414 B2 | 7/2012 | Bettuchi et al. |
| 8,210,416 B2 | 7/2012 | Milliman et al. |
| 8,256,654 B2 | 9/2012 | Bettuchi et al. |
| 8,256,656 B2 | 9/2012 | Milliman et al. |
| 8,292,152 B2 | 10/2012 | Milliman et al. |
| 8,298,286 B2 | 10/2012 | Trieu |
| 8,308,041 B2 | 11/2012 | Kostrzewski |
| 8,308,042 B2 | 11/2012 | Aranyi |
| 8,308,046 B2 | 11/2012 | Prommersberger |
| 8,322,455 B2 | 12/2012 | Shelton, IV et al. |
| 8,328,061 B2 | 12/2012 | Kasvikis |
| 8,342,377 B2 | 1/2013 | Milliman et al. |
| 8,348,129 B2 | 1/2013 | Bedi et al. |
| 8,439,936 B2 | 5/2013 | McClellan |
| 8,453,905 B2 | 6/2013 | Holcomb et al. |
| 8,453,910 B2 | 6/2013 | Bettuchi et al. |
| 8,464,925 B2 | 6/2013 | Hull et al. |
| 8,469,252 B2 | 6/2013 | Holcomb et al. |
| 8,480,692 B2 | 7/2013 | McClellan |
| 8,485,412 B2 | 7/2013 | Shelton, IV et al. |
| 8,540,131 B2 | 9/2013 | Swayze |
| 8,550,325 B2 | 10/2013 | Cohen et al. |
| 8,585,721 B2 | 11/2013 | Kirsch |
| 8,602,286 B2 | 12/2013 | Crainich et al. |
| 8,608,765 B1 | 12/2013 | Jurbala |
| 8,613,384 B2 | 12/2013 | Pastorelli et al. |
| 8,616,430 B2 | 12/2013 | (Prommersberger) Stopek |
| 8,636,766 B2 | 1/2014 | Milliman et al. |
| 8,668,130 B2 | 3/2014 | Hess et al. |
| 8,684,249 B2 | 4/2014 | Racenet et al. |
| 8,720,766 B2 | 5/2014 | Hess et al. |
| 8,740,034 B2 | 6/2014 | Morgan et al. |
| 8,801,732 B2 | 8/2014 | Harris et al. |
| 8,840,003 B2 | 9/2014 | Morgan et al. |
| 8,905,287 B2 | 12/2014 | Racenet et al. |
| 2001/0044637 A1 | 11/2001 | Jacobs et al. |
| 2001/0051815 A1 | 12/2001 | Esplin |
| 2002/0013298 A1 | 1/2002 | Hunter |
| 2002/0022861 A1 | 2/2002 | Jacobs et al. |
| 2002/0055666 A1 | 5/2002 | Hunter et al. |
| 2002/0077661 A1 | 6/2002 | Saadat |
| 2002/0123750 A1 | 9/2002 | Eisermann et al. |
| 2002/0192280 A1 | 12/2002 | Hunter et al. |
| 2003/0069602 A1 | 4/2003 | Jacobs et al. |
| 2003/0105489 A1 | 6/2003 | Eichhorn et al. |
| 2003/0153972 A1 | 8/2003 | Helmus |
| 2003/0157170 A1 | 8/2003 | Liggins et al. |
| 2003/0181371 A1 | 9/2003 | Hunter et al. |
| 2003/0203976 A1 | 10/2003 | Hunter et al. |
| 2004/0006352 A1 | 1/2004 | Nobles et al. |
| 2004/0010276 A1 | 1/2004 | Jacobs et al. |
| 2004/0060410 A1 | 4/2004 | Leung et al. |
| 2004/0076672 A1 | 4/2004 | Hunter et al. |
| 2004/0088003 A1 | 5/2004 | Leung et al. |
| 2004/0193217 A1 | 9/2004 | Lubbers et al. |
| 2004/0199241 A1 | 10/2004 | Gravett et al. |
| 2004/0219214 A1 | 11/2004 | Gravett et al. |
| 2004/0220591 A1 | 11/2004 | Bonutti |
| 2004/0224023 A1 | 11/2004 | Hunter et al. |
| 2004/0267362 A1 | 12/2004 | Hwang et al. |
| 2005/0152941 A1 | 7/2005 | Hunter et al. |
| 2005/0175665 A1 | 8/2005 | Hunter et al. |
| 2005/0186261 A1 | 8/2005 | Avelar et al. |
| 2005/0192428 A1 | 9/2005 | Berg et al. |
| 2005/0197699 A1 | 9/2005 | Jacobs et al. |
| 2006/0127445 A1 | 6/2006 | Hunter et al. |
| 2006/0135994 A1 | 6/2006 | Ruff et al. |
| 2006/0149349 A1 | 7/2006 | Garbe |
| 2006/0240064 A9 | 10/2006 | Hunter et al. |
| 2006/0240113 A1 | 10/2006 | Hunter et al. |
| 2007/0021779 A1 | 1/2007 | Garvin et al. |
| 2007/0026043 A1 | 2/2007 | Guan et al. |
| 2007/0027527 A1 | 2/2007 | Williams et al. |
| 2007/0065663 A1 | 3/2007 | Trull et al. |
| 2007/0196421 A1 | 8/2007 | Hunter et al. |
| 2007/0208355 A1 | 9/2007 | Ruff |
| 2007/0208377 A1 | 9/2007 | Kaplan et al. |
| 2008/0003394 A1 | 1/2008 | Eke |
| 2008/0027443 A1 | 1/2008 | Lambert |
| 2008/0027445 A1 | 1/2008 | Brown, Jr. et al. |
| 2008/0027446 A1 | 1/2008 | Stone et al. |
| 2008/0027486 A1 | 1/2008 | Jones et al. |
| 2008/0051888 A1 | 2/2008 | Ratcliffe et al. |
| 2008/0058579 A1 | 3/2008 | Hunter et al. |
| 2008/0124400 A1 | 5/2008 | Liggins et al. |
| 2008/0234731 A1 | 9/2008 | Leung et al. |
| 2008/0247987 A1 | 10/2008 | Liggins et al. |
| 2008/0312315 A1 | 12/2008 | Daniloff et al. |
| 2009/0012560 A1 | 1/2009 | Hunter et al. |
| 2009/0018577 A1 | 1/2009 | Leung et al. |
| 2009/0048537 A1 | 2/2009 | Lydon et al. |
| 2009/0060973 A1 | 3/2009 | Hunter et al. |
| 2009/0107965 A1 | 4/2009 | D'Agostino |
| 2009/0112259 A1 | 4/2009 | D'Agostino |
| 2009/0117070 A1 | 5/2009 | Daniloff et al. |
| 2009/0125094 A1 | 5/2009 | Rust |
| 2009/0143819 A1 | 6/2009 | D'Agostino |
| 2009/0156980 A1 | 6/2009 | Eaton et al. |
| 2009/0216326 A1 | 8/2009 | Hirpara et al. |
| 2009/0222039 A1 | 9/2009 | Dreyfuss et al. |
| 2009/0226500 A1 | 9/2009 | Avelar et al. |
| 2009/0228021 A1 | 9/2009 | Leung |
| 2009/0280153 A1 | 11/2009 | Hunter et al. |
| 2009/0324720 A1 | 12/2009 | He et al. |
| 2010/0016872 A1 | 1/2010 | Bayon et al. |
| 2010/0160718 A1 | 6/2010 | Villafana et al. |
| 2010/0217314 A1 | 8/2010 | Holsten et al. |
| 2011/0125287 A1* | 5/2011 | Hotter .............. A61B 17/06166 623/23.72 |
| 2011/0155787 A1 | 6/2011 | Baxter, III et al. |
| 2011/0301706 A1 | 12/2011 | Brooks et al. |
| 2013/0131781 A1 | 5/2013 | Greenhalgh et al. |
| 2013/0144310 A1 | 6/2013 | Gordon et al. |

OTHER PUBLICATIONS

Leung et al., "Barbed, Bi-Directional Medical Sutures: Biomechanical Properties and Wound Closure Efficacy Study," Society for Biomaterials 28ths Annual Meeting Transactions, 2002, p. 724.

Chunfeng et al., "Enhancing the Strength of the Tendon-Suture Interface Using 1-Ethyl-3-(3-dimethylaminoproply) Carbodimide Hydrochloride and Cyanoacrylate," Journal of Hand Surger, 2007, 32(5): 606-11.

Burkhead et al., "Use of Graft Jacket as an Augmentation for Massive Rotator Cuff Tears," Semin Arthro, 2007, 18 (1): 11-18.

Hirpara et al., "A Barbed Device for Digital Flexor Tendon Repair," http://proceedings.jbjs.org.uk/cgi/content/abstract/92-B/SUPP_II/291-d, Mar. 2010.

International Search Report dated Jul. 20, 2015 for International Application No. PCT/US2015/020231 (10 pages).

* cited by examiner

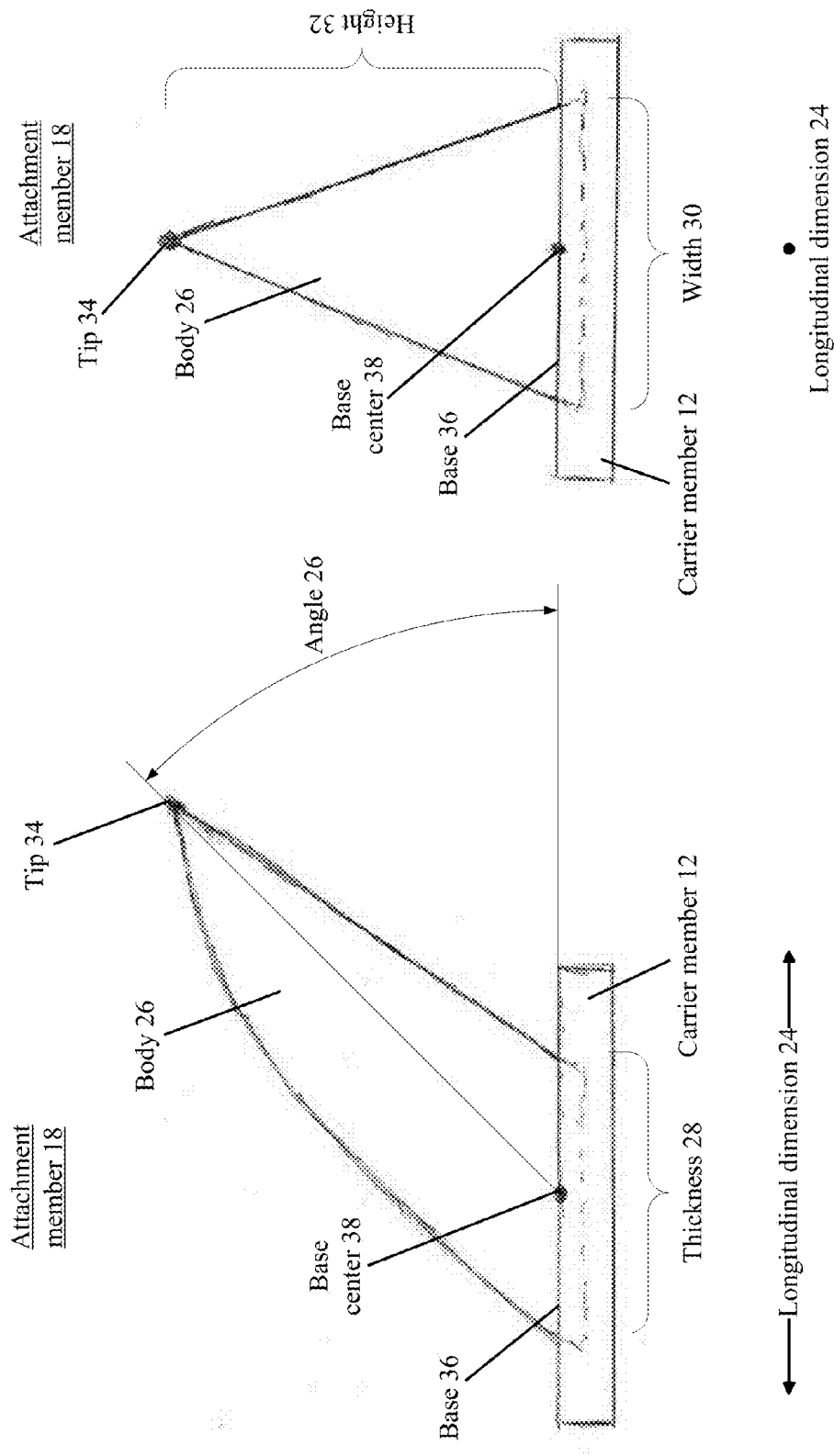

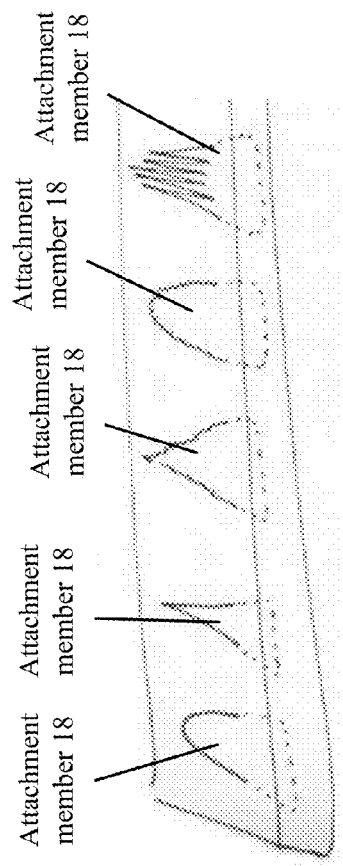
FIG. 3A
FIG. 3B
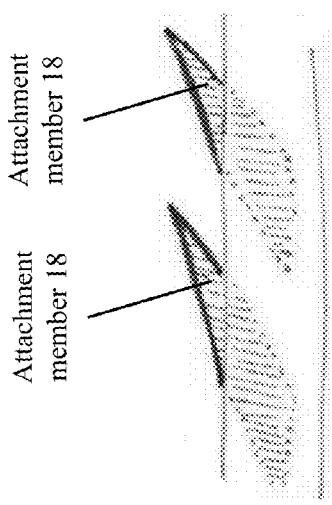
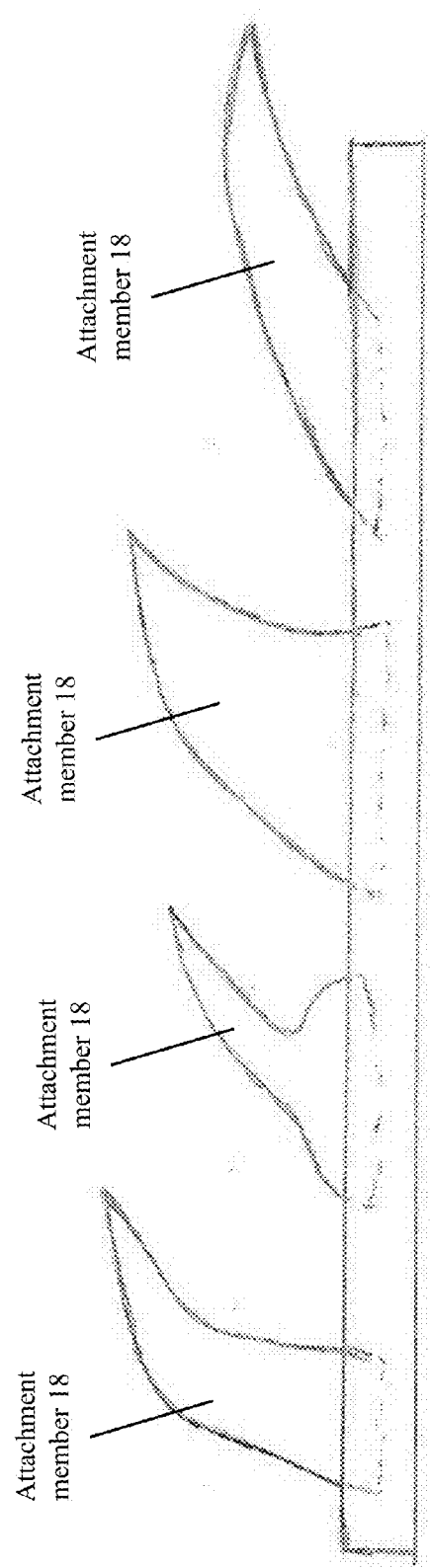
FIG. 3C

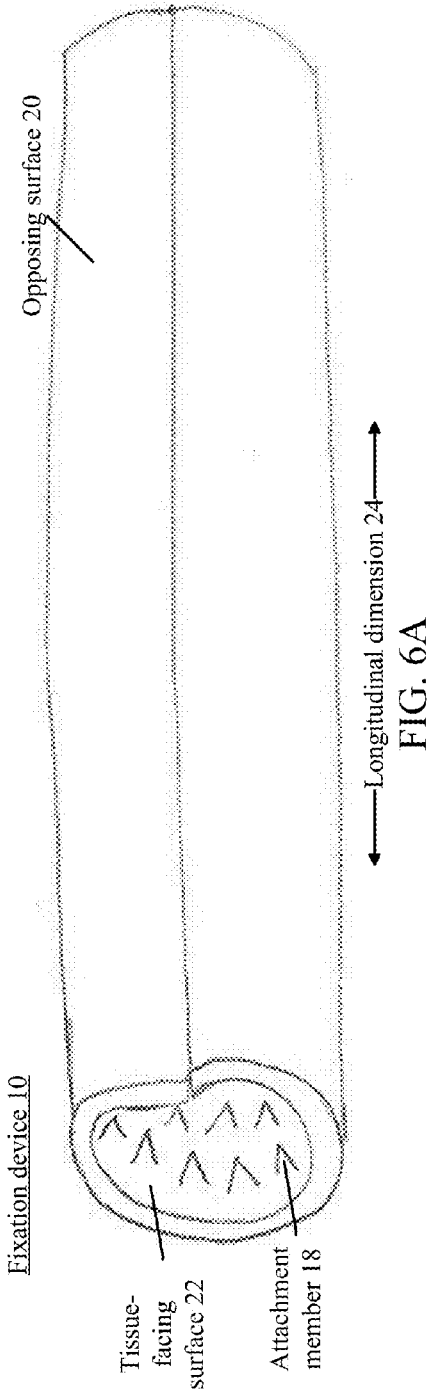
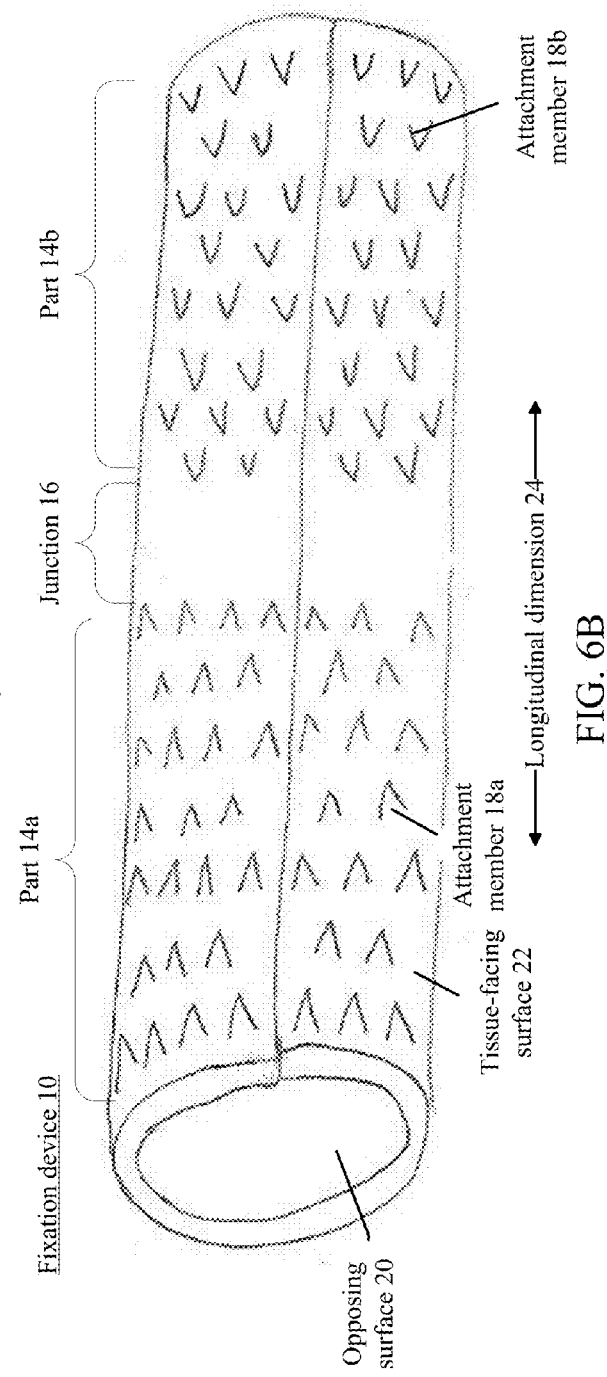
FIG. 6A
FIG. 6B

700

| affixing a fixation device to a first portion of connective tissue and a second portion of connective tissue
702 |

--- providing a fixation device comprising a carrier member having a first part, a second part, and a junction therebetween
902

--- advancing, when the carrier member is conformed into the cylindrical structure, the first portion through the first opening into the interior of the cylindrical structure until a tip of the first portion reaches the junction such that the one or more first attachment members engage the first portion
904

--- advancing, when the carrier member is conformed into the cylindrical structure, the second portion through the second opening into the interior of the cylindrical structure until a tip of the second portion reaches the junction such that the one or more second attachment members engage the second portion
906

FIG. 9

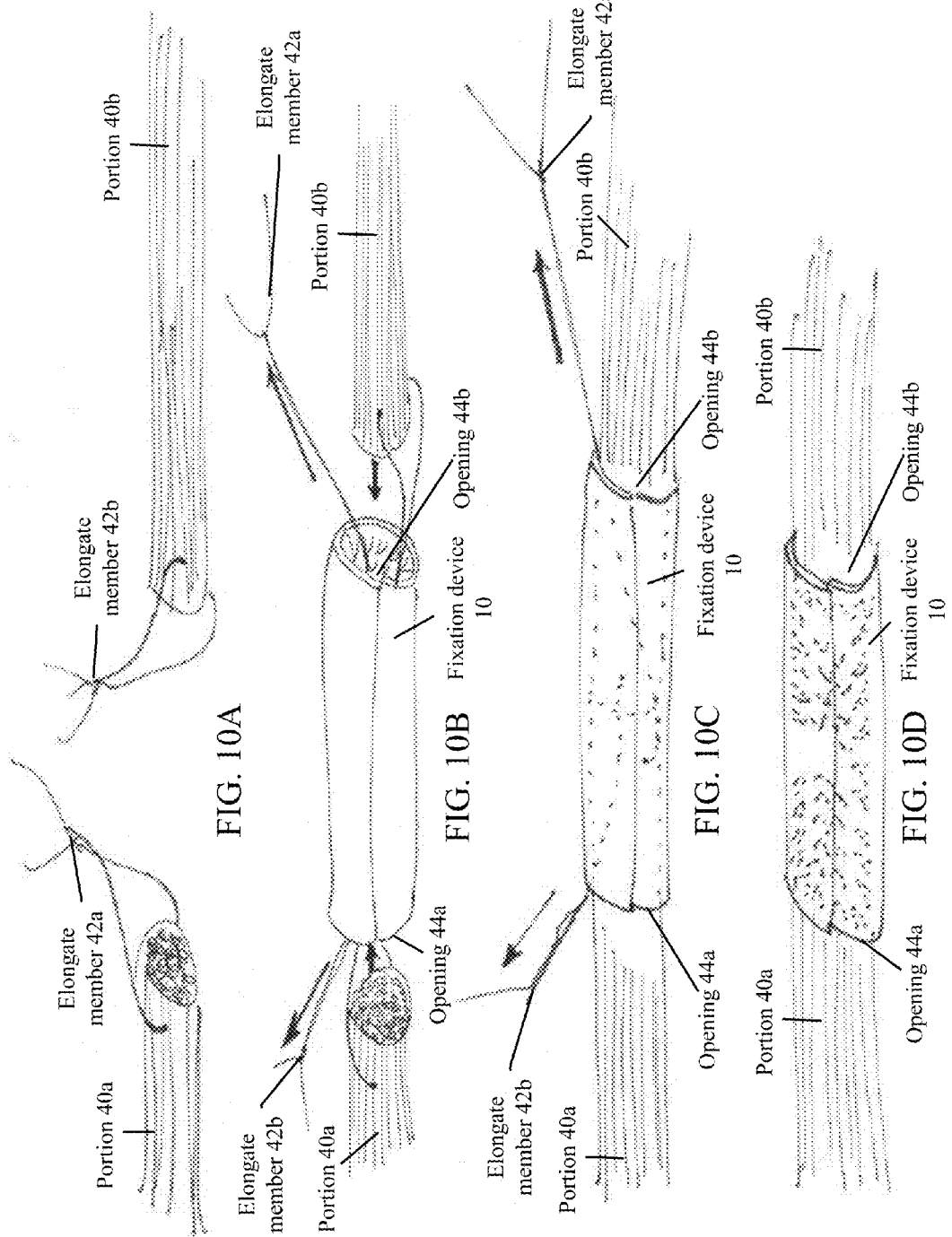

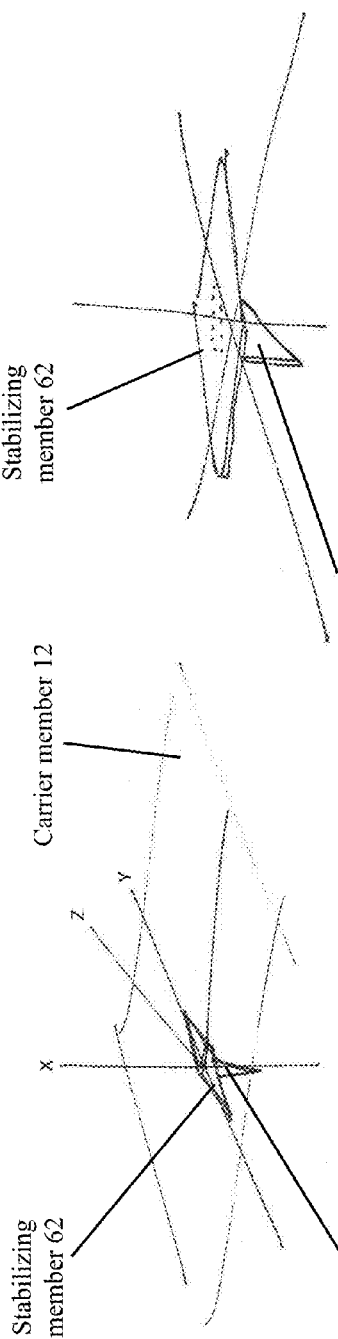
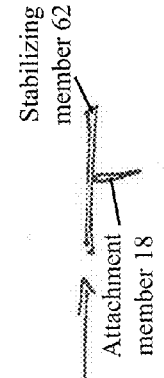
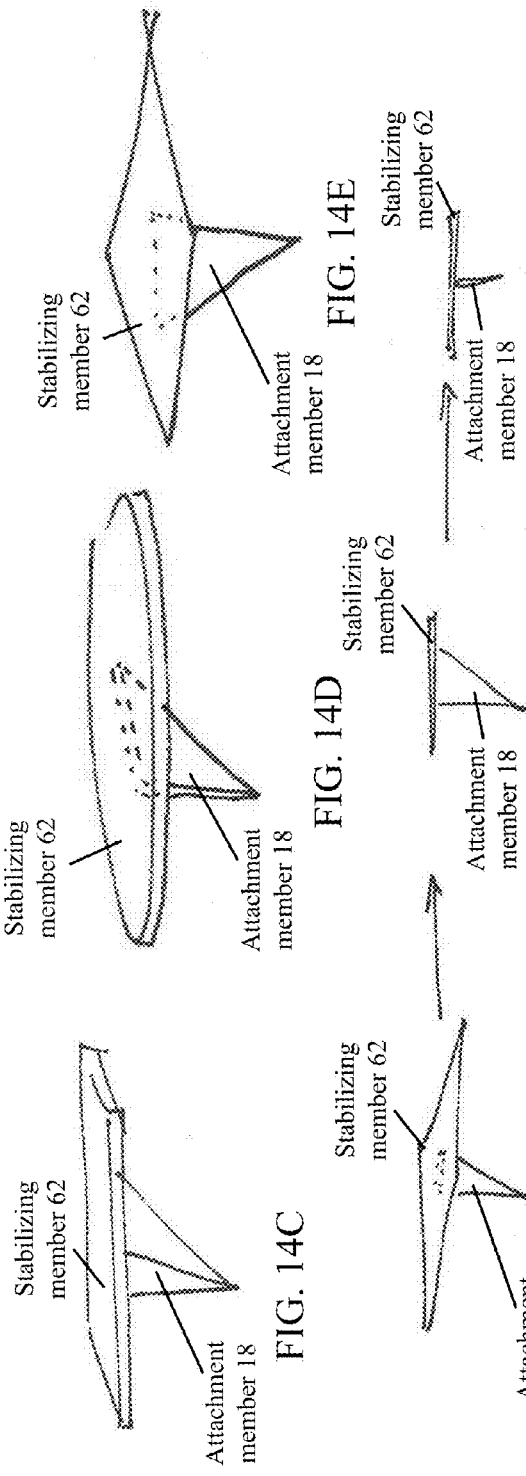

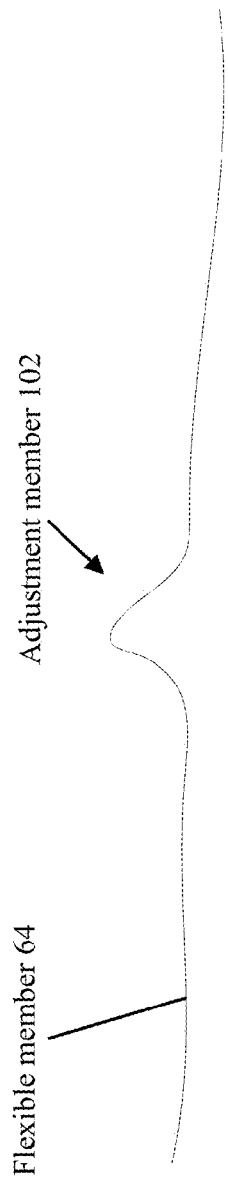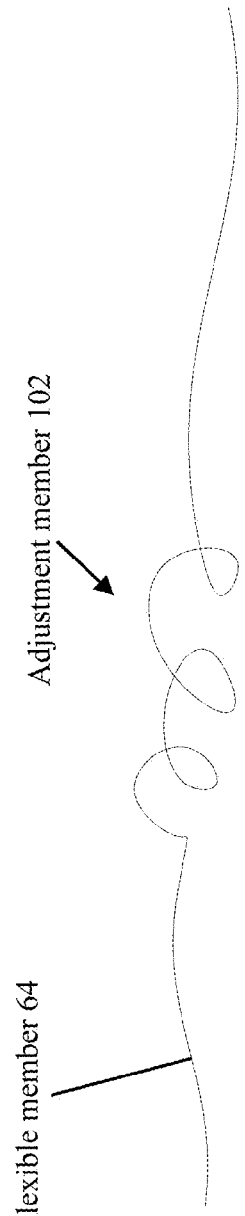
FIG. 16B
FIG. 16C

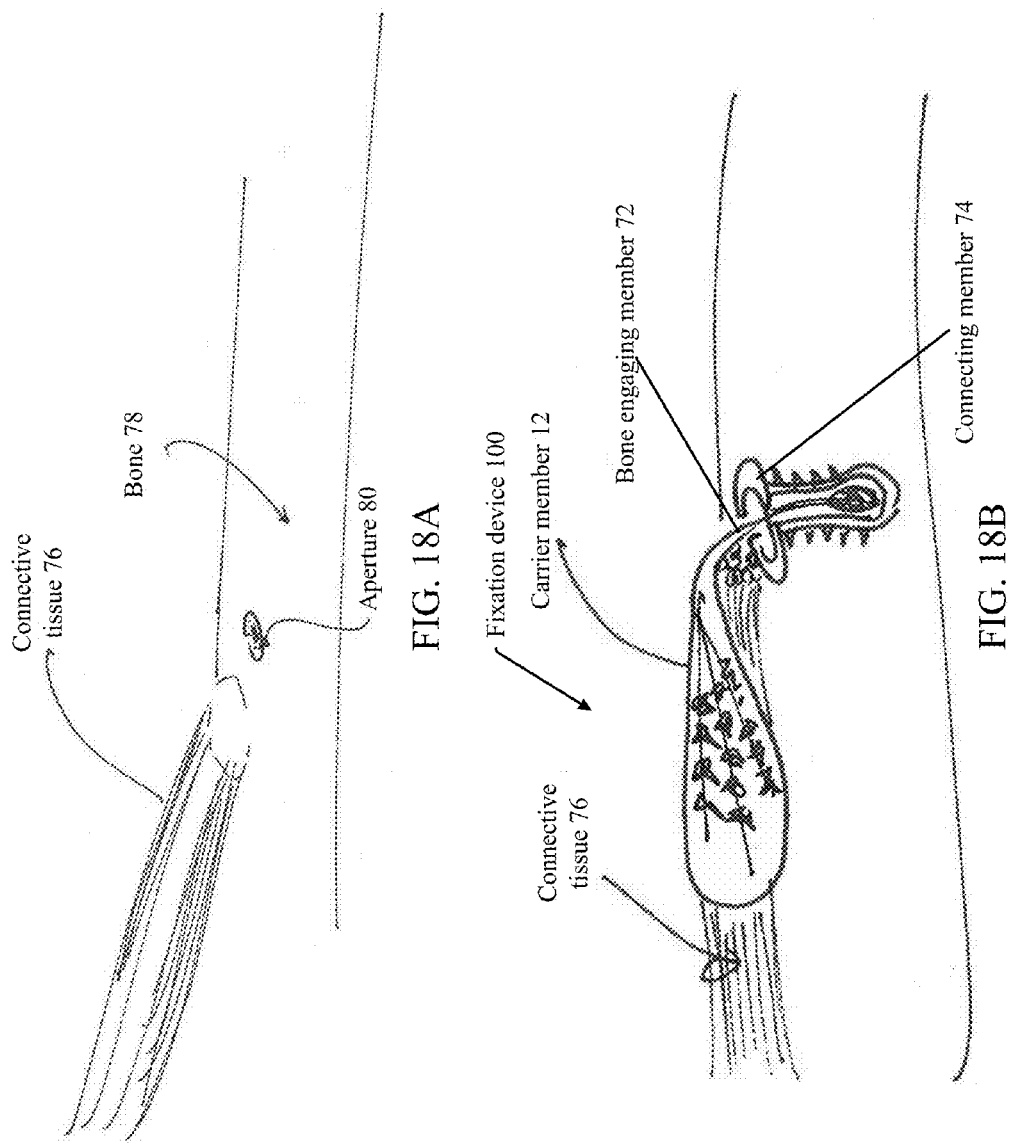

SYSTEM FOR TISSUE FIXATION TO BONE

CROSS-REFERENCE TO RELATED APPLICATIONS

The present application is a divisional of U.S. patent application Ser. No. 13/021,651, filed Feb. 4, 2011, the disclosure of which is hereby incorporated by reference in its entirety.

TECHNICAL FIELD

The present invention generally relates to tissue fixation.

BACKGROUND

Lacerated flexor tendon repair is a procedure performed approximately 145,000 times a year in the United States alone. Early post operative mobilization is beneficial to restoring maximal tendon function following injury and repair. Adhesion formation is a common complication following tendon repair, but can be reduced through motion rehabilitation programs. By preventing adhesion formation and gliding resistance, tendon healing may be enhanced. However, the failure rate of tendon repairs is close to 30 percent, primarily because of overloading at the repair site. Although an objective of tendon repair is to provide adequate strength for passive and active motion during rehabilitation, it is important to maintain a delicate balance between rehabilitative motion protocols and fatiguing the repair site.

A procedure for lacerated tendon repair is to use suture to mend the two ends of a tendon together using complex suture patterns. While this provides a good initial repair, the strength and quality of the repair may quickly degrade with subsequent loading and mobilization. Although postoperative therapy may be utilized to reduce adhesion, the resulting tension can induce gap formation or tendon rupture at the repair site, seriously impairing the outcome of the repair. Gapping at the repair site has many negative effects, such as reduced repair strength, tendon rupture, and an increased probability for adhesion.

BRIEF SUMMARY OF THE INVENTION

According to various embodiments of the subject disclosure, an apparatus for fixating connective tissue is provided. The apparatus may comprise a carrier member having a first part, a second part, and a junction therebetween. The carrier member may be configured to encompass, at least in part, an interior space. The apparatus may also comprise one or more first attachment members protruding into the interior space and at a first angle from the first part toward the junction. The one or more first attachment members may be configured to engage a first portion of connective tissue in the interior space for attaching the first part to the first portion. The apparatus may comprise one or more second attachment members protruding from the second part into the interior space. The one or more second attachment members may be configured to engage a second portion of connective tissue in the interior space for attaching the second part to the second portion. In some embodiments, when the first part is attached to the first portion and the second part is attached to the second portion, the first portion and the second portion are limited in being pulled apart from one another during physiological use of the connective tissue.

In some embodiments, the carrier member has a length, width, and thickness. The length and width may each be at least two times, three times, four times, five times, eight times, ten times, 15 times, 20 times, 25 times, 50 times, 100 times, or 200 times greater than the thickness.

In some embodiments, the one or more second attachment members protrude at a second angle from the second part toward the junction. In some embodiments, at least one of the first angle and the second angle is less than or equal to about 5 degrees, 10 degrees, 15 degrees, 20 degrees, 30 degrees, 40 degrees, 45 degrees, 50 degrees, 65 degrees, 75 degrees, or 85 degrees. The first angle and the second angle are of about the same magnitude.

In certain embodiments, an average thickness of at least one of the one or more first attachment members is such that when the first part is attached to the first portion, the first angle is maintained at less than about 5 degrees, 10 degrees, 15 degrees, 20 degrees, 30 degrees, 40 degrees, 45 degrees, 50 degrees, 65 degrees, 75 degrees, 85 degrees, or 90 degrees during physiological use of the connective tissue. The average thickness may be measured along a direction substantially parallel to a longitudinal dimension of the carrier member.

In some embodiments, at least one of the one or more first attachment members comprises at least one of a hook, a barb, and a pin. In some embodiments, at least one of the one or more first attachment members is less elastic than is the carrier member.

In certain embodiments, an average height of at least one of the one or more first attachment members is greater than about 6 millimeters, between about 6 and 4 millimeters, between about 4 millimeters and 2 millimeters, between about 2 millimeters and 1.75 millimeters, between about 1.75 millimeters and 1.50 millimeters, between about 1.50 millimeters and about 1.25 millimeters, between about 1.25 millimeters and about 1 millimeter, between about 1 millimeter and about 0.75 millimeter, between about 0.75 millimeter and about 0.5 millimeter, between about 0.5 millimeter and about 0.25 millimeter, between about 0.25 millimeter and about 0.10 millimeter, between about 0.10 millimeter and about 0.075 millimeter, between about 0.075 millimeter and about 0.05 millimeter, between about 0.05 millimeter and about 0.025 millimeter, between about 0.025 millimeter and about 0.01 millimeter, or less than about 0.01 millimeter.

In some embodiments, the first part comprises a tissue-facing surface that faces the connective tissue when the first part engages the first portion. The first part and each of the one or more first attachment members may meet at a respective base having an area. A ratio of the total area of all the bases to the total area of the tissue-facing surface may be greater than or equal to about 0.05, 0.10, 0.20, 0.30, 0.40, 0.50, 0.60, 0.70, 0.80, 0.90, or 0.95.

In certain embodiments, a ratio of a greatest width of a base of a first attachment member to an average height of the first attachment member is greater than or equal to about 1.4, between about 1.4 and 1.2, between about 1.2 and 1.0, between about 1.0 and 0.95, between about 0.95 and about 0.90, between about 0.90 and about 0.80, between about 0.80 and about 0.70, between about 0.70 and about 0.60, between about 0.60 and about 0.50, between about 0.50 and about 0.40, between about 0.40 and about 0.30, between about 0.30 and about 0.20, between about 0.20 and about 0.10, or less than or equal to about 0.05. The greatest width may be measured along a direction substantially perpendicular to a longitudinal dimension of the base and substantially parallel to the tissue-facing surface. The longitudinal dimension of the base may be a direction the first attachment member is protruding toward in substantially the same plane as the base.

In some embodiments, at least three of the one or more first attachment members are arranged with respect to the carrier member in at least one of a grid-like array and a staggered array. In some embodiments, at least one of the first attachment members comprises a polymer. In some embodiments, at least one of the first attachment members comprises non-polymeric resorbable biomaterials including calcium-based ceramics (e.g., calcium phosphates, various hydroxyapatites, carbonates or sulfates), biocompatible silicates (e.g., bioglasses), silicon or titanium nitrides or oxides, or their composites with degradable polymers (e.g., biomedical grade degradable or non-degradable polyester or polyurethane). In some embodiments, at least one of the one or more first attachment members comprise at least one of a thermoplastic, ultraviolet curable resin, biodegradable polyester, polycarbonate urethane, and polyurethane (e.g., programmed degradable polyurethane). These materials may be medical grade. The biodegradable polyester may comprise at least one of polycaprolactone, poly(L-lactide), poly(D,L-lactide), and poly(glycolide-co-lactide). The molecular weight of the polycaprolactone may be between about 150,000 and 250,000 and the molecular weight of the poly(L-lactide), poly(D,L-lactide), or poly(glycolide-co-lactide) is between about 150,000 and 250,000. In some embodiments, the molecular weight of the polycaprolactone may be less than about 150,000 and the molecular weight of the poly(L-lactide), poly(D,L-lactide), or poly(glycolide-co-lactide) may be less than about 150,000. In some embodiments, the molecular weight of the polycaprolactone may be greater than about 250,000 and the molecular weight of the poly(L-lactide), poly(D,L-lactide), or poly(glycolide-co-lactide) may be greater than about 250,000.

In some embodiments, the carrier member comprises an elastomer (e.g., medical grade). In some embodiments, the carrier member comprises at least one of an ultraviolet curable resin, methacrylated polybutadiene, polyester urethane, polycarbonate polyurethane, polyether urethane, silicone rubber, nitrile rubber, polyphosphazene, and acrylic copolymer. These materials may be medical grade. In some embodiments, the carrier member comprises a degradable elastomer with programmed mechanical properties to match the tissue mechanical and healing requirements. In some embodiments, the carrier member comprises at least one of a bioactive or pharmacologically active agent (e.g., to facilitate tissue repair and function), an anti-inflammatory material, an anti-fibrotic material, an anti-thrombotic material, growth-enhancing or promoting material, and an anti-biotic material, within, released from, or on the carrier member. At least part of the carrier member may be hydrophilic, wettable by water and body fluids. In some embodiments, at least part of the carrier member may be hydrophilic, wetting, and lubricious. In some embodiments, at least part of the carrier member comprises a swellable material. The swellable material may comprise a hydrogel of either synthetic or biopolymer chemistry. In some embodiments, the swellable material comprises a polymer hydrogel. In some embodiments, the carrier member comprises a sheet. In some embodiments, the sheet may be flexible. In some embodiments, the carrier member is substantially flat.

In some embodiments, at least one of the carrier member, the one or more first attachment members, and the one or more second attachment members comprise biodegradable material. The biodegradable material may comprise at least one of biodegradable polyester, polyanhydride, polytyrosine, fibrin glue, and polyamide. In some embodiments, at least one of the carrier member, the one or more first attachment members, and the one or more second attachment members comprises a shape memory material that can be degradable or non-degradable by design. The biodegradable polyester may comprise at least one of polycaprolactone, poly(L-lactide), poly(D,L-lactide), and poly(glycolide-co-lactide). The molecular weight of the polycaprolactone may be between about 150,000 and 250,000 and the molecular weight of the poly(L-lactide), poly(D,L-lactide), or poly(glycolide-co-lactide) may be between about 150,000 and 250,000. In some embodiments, the molecular weight of the polycaprolactone may be less than about 150,000 and the molecular weight of the poly(L-lactide), poly(D,L-lactide), or poly(glycolide-co-lactide) may be less than about 150,000. In some embodiments, the molecular weight of the polycaprolactone may be greater than about 250,000 and the molecular weight of the poly(L-lactide), poly(D,L-lactide), or poly(glycolide-co-lactide) may be greater than about 250,000. In some embodiments, at least one of the one or more first attachment members and the one or more second attachment members is configured to transform from a non-engaging configuration to an engaging configuration upon application of a stimulus. In some embodiments, the stimulus comprises at least one of light, heat, and moisture (e.g., aqueous moisture). In some embodiments, the stimulus comprises at least one of light, heat, and organic solvents.

In some embodiments, at least one of (a) the carrier member and (b) at least one of the first attachment members comprises a pharmacology active connective tissue growth promoter or factor. In some embodiments, at least one of (a) the carrier member and (b) at least one of the first attachment members comprises a bioactive connective tissue growth factor. At least part of the carrier member may be permeable or porous. In certain embodiments, at least part of the carrier member comprises a lattice design. At least one of the one or more first attachment members and the one or more second attachment members may protrude from an intersection point of the lattice design. In certain embodiments, the carrier member is flexible such that the carrier member can conform to the connective tissue.

In some embodiments, the carrier member is configured to conform into a cylindrical structure such that a first opening is formed at the first part, a second opening is formed at the second part, and the junction is disposed between the first opening and the second opening. In certain embodiments, a first rim is formed at the first opening and a second rim is formed at the second opening. The one or more first attachment members may protrude from the first rim in an interior of the cylindrical structure and the one or more second attachment members may protrude from the second rim in the interior of the cylindrical structure. In some embodiments, the first portion comprises at least one of a ligament and a tendon. In some embodiments, the first portion and the second portion are of the same connective tissue type.

According to various embodiments of the subject disclosure, a method for fixating connective tissue is provided. The method may comprise affixing a fixation device to a first portion of connective tissue and a second portion of connective tissue. The fixation device comprises a carrier member having a first part, a second part, and a junction therebetween. The carrier member may be configured to encompass, at least in part, an interior space. The fixation device further comprises one or more first attachment members protruding into the interior space and at a first angle from the first part toward the junction. The one or more first attachment members may be configured to engage the first portion in the interior space for attaching the first part to the first portion. The fixation device further comprises one or more second attachment members protruding from the second part into the interior space. The one or more second attachment members may be configured to engage the second portion in the interior space for attaching the second part to the second portion. The fixation device is affixed to the first portion and the second portion such that (a) the first part conforms to the first portion and the one or more first attachment members engage the first portion, (b) the second part conforms to the second portion and the one or more second attachment members engage the second portion, and (c) the junction is disposed approximately between the first portion and the second portion. When the first part is attached to the first portion and the second part is attached to the second portion, the first portion and the second portion are held reliably within the fixation device and limited in being pulled apart from one another during physiological use of the connective tissue.

In some embodiments, the carrier member has a length, width, and thickness. The length and width may each be at least two times, three times, four times, five times, eight times, ten times, 15 times, 20 times, 25 times, 50 times, 100 times, or 200 times greater than the thickness.

In some embodiments, the method further comprises coupling the first portion to the second portion. The coupling may comprise attaching the first portion to the second portion with at least one of a suture, staple, pin, tack, surgical adhesive or glue, and thermal bond. In some embodiments, the affixing further comprises transforming at least one of the one or more first attachment members and the one or more second attachment members from a non-engaging configuration to an engaging configuration. In some embodiments, the transforming comprises applying a stimulus to at least one of the one or more first attachment members and the one or more second attachment members. The stimulus may comprise at least one of light, heat and, moisture (e.g., aqueous moisture). In some embodiments, the stimulus may comprise at least one of light, heat, and organic solvents.

According to various embodiments of the subject disclosure, a method for fixating connective tissue is provided. The method comprises providing a fixation device comprising a carrier member having a first part, a second part, and a junction therebetween. The fixation device further comprises one or more first attachment members protruding at a first angle from the first part toward the junction. The one or more first attachment members may be configured to engage a first portion of connective tissue for attaching the first part to the first portion. The fixation device further comprises one or more second attachment members protruding from the second part. The one or more second attachment members may be configured to engage a second portion of connective tissue for attaching the second part to the second portion. The carrier member is configured to conform into a cylindrical structure such that a first opening is formed at the first part, a second opening is formed at the second part, the junction is disposed between the first opening and the second opening, the one or more first attachment members protrude from the first part in an interior of the cylindrical structure, and the one or more second attachment members protrude from the second part in the interior of the cylindrical structure.

The method also comprises advancing, when the carrier member is conformed into the cylindrical structure, the first portion through the first opening into the interior of the cylindrical structure until a tip of the first portion reaches the junction such that the one or more first attachment members engage the first portion. The method also comprises advancing, when the carrier member is conformed into the cylindrical structure, the second portion through the second opening into the interior of the cylindrical structure until a tip of the second portion reaches the junction such that the one or more second attachment members engage the second portion. When the first part is attached to the first portion and the second part is attached to the second portion, the first portion and the second portion are limited in being pulled apart from one another during physiological use of the connective tissue.

In some embodiments, the method may further comprise conforming the carrier member into the cylindrical structure. In some embodiments, the advancing the first portion comprises coupling the tip of the first portion to a first suture and advancing the first suture through the first opening into the interior of the cylindrical structure such that the first portion is drawn into the interior of the cylindrical structure through the first opening. In some embodiments, the advancing the second portion comprises coupling the tip of the second portion to a second suture and advancing the second suture through the second opening into the interior of the cylindrical structure such that the second portion is drawn into the interior of the cylindrical structure through the second opening. In some embodiments, the method further comprises transforming at least one of the one or more first attachment members and the one or more second attachment members from a non-engaging configuration to an engaging configuration. In some embodiments, the transforming comprises applying a stimulus to at least one of the one or more first attachment members and the one or more second attachment members. The stimulus may comprise at least one of light, heat, and moisture (e.g., aqueous moisture). In some embodiments, the stimulus may comprise at least one of light, heat, and organic solvents.

According to various embodiments of the subject disclosure, an apparatus for stabilizing connective tissue is provided. The apparatus comprises a carrier member having a length, width, and thickness. In some embodiments, the length and width may each be at least two times, three times, four times, five times, eight times, ten times, 15 times, 20 times, 25 times, 50 times, 100 times, or 200 times greater than the thickness. The apparatus also comprises a plurality of attachment members extending from the carrier member and configured to engage connective tissue. The apparatus also comprises a plurality of stabilizing members, each configured to couple a respective attachment member to the carrier member. Each stabilizing member is substantially positionally fixed relative to the carrier member.

In some embodiments, each stabilizing member is configured to resist angular motion of a respective attachment member relative to the carrier member. In some embodiments, each stabilizing member resides at least partially in the carrier member. According to certain embodiments, each stabilizing member is substantially parallel to a face of the carrier member. In some embodiments, each stabilizing member is substantially perpendicular to a respective attachment member. In some embodiments, each stabilizing member is integral with a respective attachment member. Each stabilizing member may form a base of a respective attachment member. In some embodiments, a length of each stabilizing member is greater than or equal to a height of a respective attachment member. In some embodiments, each attachment member is configured to penetrate at least partially the connective tissue. Each attachment member may extend substantially perpendicular from a respective stabilizing member.

According to certain embodiments, the apparatus also comprises a first flexible member connecting a first set of the plurality of attachment members. The first flexible member comprises at least one of a fiber, a filament, a string, a thread, and a line. The first flexible member comprises at least one of polyethelene, poly glycolic acid, and nylon. In some embodiments, the first flexible member resides at least partially in the carrier member. In some embodiments, the first flexible member resides at least partially in a stabilizing member coupled to a respective attachment member of the first set of the plurality of attachment members.

In some embodiments, an elasticity of at least one of the first flexible member and the carrier member is substantially the same as an elasticity of the connective tissue. In some embodiments, an elasticity of at least one of the first flexible member and the carrier member is slightly greater than an elasticity of the connective tissue. In some embodiments, the first flexible member comprises an adjustment member configured to resize a length of the first flexible member. In some embodiments, the adjustment member comprises at least one of a coil, a curve, and a kink. In some embodiments, the adjustment member is configured to resize the length of the first flexible member such that the length of the first flexible member is substantially the same as a length of the connective tissue during physiological use of the connective tissue.

In some embodiments, the apparatus also comprises a second flexible member connecting a second set of the plurality of attachment members. The first set of the plurality of attachment members is aligned with the second set of the plurality of attachment members such that a long axis of the first set of the plurality of attachment members is substantially parallel to a long axis of the second set of the plurality of attachment members.

According to various embodiments of the subject disclosure, the carrier member has a first part, a second part, and a junction therebetween. The carrier member is configured to encompass, at least partially, an interior space. The plurality of attachment members comprises one or more first attachment members extending into the interior space and at a first angle from the first part toward the junction. The one or more first attachment members is configured to engage a first portion of connective tissue in the interior space for attaching the first part to the first portion. The plurality of attachment members comprises one or more second attachment members extending from the second part into the interior space. The one or more second attachment members is configured to engage a second portion of connective tissue in the interior space for attaching the second part to the second portion. In some embodiments, when the first part is attached to the first portion and the second part is attached to the second portion, the first portion and the second portion are limited in being pulled apart from one another during physiological use of the connective tissue.

According to various embodiments of the subject disclosure, a method for stabilizing connective tissue is provided. The method comprises affixing a fixation device to connective tissue. The fixation device comprises a carrier member having a length, width, and thickness, the length and width each being at least two times, three times, four times, five times, eight times, ten times, 15 times, 20 times, 25 times, 50 times, 100 times, or 200 times greater than the thickness. The fixation device further comprises a plurality of attachment members extending from the carrier member and configured to engage connective tissue. The fixation device further comprises a plurality of stabilizing members, each configured to couple a respective attachment member to the carrier member. In some embodiments, during the affixing, each stabilizing member resists angular motion of a respective attachment member relative to the carrier member.

In some embodiments, each stabilizing member resides at least partially in the carrier member. In some embodiments, the fixation device further comprises a flexible member connecting a first set of the plurality of attachment members. In some embodiments, an elasticity of at least one of the flexible member and the carrier member is substantially the same as an elasticity of the connective tissue. In some embodiments, an elasticity of at least one of the flexible member and the carrier member is slightly greater than an elasticity of the connective tissue. In some embodiments, the method further comprises resizing a length of the flexible member. In some embodiments, the method further comprises resizing a length of the flexible member such that the length of the flexible member is substantially the same as a length of the connective tissue during physiological use of the connective tissue.

In some embodiments, the fixation device is affixed to a first portion of connective tissue and a second portion of connective tissue. The carrier member has a first part, a second part, and a junction therebetween. In some embodiments, after the affixing, the carrier member is configured to encompass, at least partially, an interior space. The plurality of attachment members comprises one or more first attachment members extending into the interior space and at a first angle from the first part toward the junction. The one or more first attachment members is configured to engage the first portion in the interior space for attaching the first part to the first portion. The plurality of attachment members comprises one or more second attachment members extending from the second part into the interior space. The one or more second attachment members is configured to engage the second portion in the interior space for attaching the second part to the second portion. In some embodiments, the fixation device is affixed to the first portion and the second portion such that (a) the first part conforms to the first portion and the one or more first attachment members engage the first portion, (b) the second part conforms to the second portion and the one or more second attachment members engage the second portion, and (c) the junction is disposed approximately between the first portion and the second portion. In some embodiments, when the first part is attached to the first portion and the second part is attached to the second portion, the first portion and the second portion are limited in being pulled apart from one another during physiological use of the connective tissue.

According to various embodiments of the subject disclosure, a method for stabilizing connective tissue. The method comprises providing a fixation device comprising a carrier member having a first part, a second part, and a junction therebetween. The carrier member having a length, width, and thickness, the length and width each being at least two times, three times, four times, five times, eight times, ten times, 15 times, 20 times, 25 times, 50 times, 100 times, or 200 times greater than the thickness. The fixation device further comprises a plurality of attachment members extending from the carrier member and configured to engage connective tissue. The fixation device further comprises a plurality of stabilizing members, each configured to couple a respective attachment member to the carrier member. Each stabilizing member resides at least partially in the carrier member. In some embodiments, the plurality of attachment members comprises one or more first attachment members extending at a first angle from the first part toward the junction. The one or more first attachment members is configured to engage a first portion of connective tissue for attaching the first part to the first portion. The plurality of attachment members comprises one or more second attachment members extending from the second part. The one or more second attachment members is configured to engage a second portion of connective tissue for attaching the second part to the second portion.

In some embodiments, the carrier member is configured to conform into a substantially tubular structure such that a first opening is formed at the first part, a second opening is formed at the second part, the junction is disposed between the first opening and the second opening. The one or more first attachment members extend from the first part in an interior of the substantially tubular structure, and the one or more second attachment members extend from the second part in the interior of the substantially tubular structure. The method further comprises advancing, when the carrier member is conformed into the substantially tubular structure, the first portion through the first opening into the interior of the substantially tubular structure until a tip of the first portion reaches the junction such that the one or more first attachment members engage the first portion. The method further comprises advancing, when the carrier member is conformed into the substantially tubular structure, the second portion through the second opening into the interior of the substantially tubular structure until a tip of the second portion reaches the junction such that the one or more second attachment members engage the second portion. In some embodiments, during the advancing the first portion and the advancing the second portion, each stabilizing member resists angular motion of a respective attachment member relative to the carrier member. In some embodiments, when the first part is attached to the first portion and the second part is attached to the second portion, the first portion and the second portion are limited in being pulled apart from one another during physiological use of the connective tissue.

In some embodiments, the fixation device further comprises a flexible member connecting a first set of the plurality of attachment members. In some embodiments, an elasticity of at least one of the flexible member and the carrier member is substantially the same as an elasticity of the connective tissue. In some embodiments, an elasticity of at least one of the flexible member and the carrier member is slightly greater than an elasticity of the connective tissue. In some embodiments, the method further comprises resizing a length of the flexible member. In some embodiments, the method further comprises resizing a length of the flexible member such that the length of the flexible member is substantially the same as a length of the connective tissue during physiological use of the connective tissue.

According to various embodiments of the subject disclosure, an apparatus for fixating connective tissue to bone is provided. The apparatus comprises a carrier member having a length, width, and thickness. The length and width each being at least two times, three times, four times, five times, eight times, ten times, 15 times, 20 times, 25 times, 50 times, 100 times, or 200 times greater than the thickness. The apparatus comprises a plurality of attachment members extending from the carrier member and configured to engage connective tissue of an animal. The apparatus also comprises a bone engaging member extending from the carrier member and configured to attach to a bone of the animal. In some embodiments, when the plurality of attachment members is engaged with the connective tissue and the bone engaging member is attached to the bone, the connective tissue and the bone are limited in being pulled apart from one another during physiological use of the connective tissue.

In some embodiments, the carrier member and the bone engaging member are integral with one another. The connective tissue comprises at least one of a ligament and a tendon. In some embodiments, the bone engaging member is configured to be inserted into an aperture within the bone. In some embodiments, the apparatus further comprises a connecting member configured to be inserted into an aperture within the bone, where the bone engaging member is attached to the bone by being inserted into the connecting member when the connecting member is inserted into the aperture within the bone.

According to certain embodiments, the connecting member comprises a first wall, a second wall attached to the first wall at a base of the connecting member, and a cavity therebetween. The connecting member is configured such that the first wall and the second wall is displaceable relative to one another. At least one of the first wall and the second wall is configured to be displaced relative to the base of the connecting member. The cavity comprises a neck portion and a bulge portion. In some embodiments, the bulge portion is positioned at the base of the connecting member and has a larger volume than the neck portion when the first wall and the second wall are not displaced relative to one another. In some embodiments, the bone engaging member comprises a tip portion sized to fit within the bulge portion of the cavity of the connecting member. The bone engaging member comprises an elongate portion sized to fit within the neck portion of the cavity when the first wall and the second wall are not displaced relative to one another. In some embodiments, an outer surface of the first wall comprises a plurality of threads configured to engage an inner surface of the aperture within the bone.

According to certain embodiments, the carrier member comprises a sheet. In some embodiments, the carrier member comprises at least one of a leaf shape, a tear drop shape, and a fusiform shape. The carrier member is configured to wrap around the connective tissue. The carrier member is configured to conform to the connective tissue. The apparatus also comprises a plurality of stabilizing members each configured to couple a respective attachment member to the carrier member. Each stabilizing member is substantially positionally fixed relative to the carrier member. In some embodiments, each stabilizing member is configured to resist angular motion of a respective attachment member relative to the carrier member. In some embodiments, each stabilizing member resides at least partially in the carrier member.

According to certain embodiments, the apparatus further comprises a first flexible member connecting a first set of the plurality of attachment members. The first flexible member resides at least partially in the carrier member. The apparatus further comprises a second flexible member connecting a second set of the plurality of attachment members. In some embodiments, the first set of the plurality of attachment members is aligned with the second set of the plurality of attachment members such that a distance between the first flexible member and the second flexible member is greater at a first half of the carrier member than at a second half of the carrier member, the second half positioned between the first half and the bone engaging member.

According to various embodiments of the subject disclosure, a method for fixating connective tissue to bone is provided. The method comprises engaging connective tissue of an animal with a plurality of attachment members extending from a carrier member. The carrier member has a length, width, and thickness. The length and width is each at least two times, three times, four times, five times, eight times, ten times, 15 times, 20 times, 25 times, 50 times, 100 times, or 200 times greater than the thickness. The method also comprises attaching a bone engaging member extending from the carrier member to a bone of the animal. In some embodiments, when the plurality of attachment members is engaged with the connective tissue and the bone engaging member is attached to the bone, the connective tissue and the bone are limited in being pulled apart from one another during physiological use of the connective tissue.

In some embodiments, attaching the bone engaging member comprises inserting the bone engaging member into an aperture within the bone. In some embodiments, attaching the bone engaging member comprises inserting a connecting member into an aperture within the bone. The connecting member comprises a first wall, a second wall attached to the first wall at a base of the connecting member, and a cavity therebetween. The connecting member is configured such that the first wall and the second wall is displaceable relative to one another. The cavity comprises a neck portion and a bulge portion. The bulge portion is positioned at a base of the connecting member. The bulge portion has a larger volume than the neck portion when the first wall and the second wall are not displaced relative to one another.

In some embodiments, attaching the bone engaging member comprises: displacing the first wall and the second wall relative to one another from a first position to a second position; inserting the bone engaging member into the aperture of the bone such that a tip portion of the bone engaging member fits within the bulge portion of the cavity; and permitting the first wall and the second wall to return toward the first position such that an elongate portion of the bone engaging member fits within the neck portion of the cavity. In some embodiments, an outer surface of the first wall comprises a plurality of threads that engage an inner surface of the aperture within the bone.

In some embodiments, the carrier member comprises a sheet. In some embodiments, the carrier member comprises at least one of a leaf shape, a tear drop shape, and a fusiform shape. The method also comprises wrapping the carrier member around the connective tissue. The method also comprises conforming the carrier member to the connective tissue. In some embodiments, a plurality of stabilizing members is each configured to couple a respective attachment member to the carrier member. In some embodiments, during the engaging, each stabilizing member resists angular motion of a respective attachment member relative to the carrier member. In some embodiments, each stabilizing member resides at least partially in the carrier member.

According to certain embodiments, a first flexible member connects a first set of the plurality of attachment members. In some embodiments, the first flexible member resides at least partially in the carrier member. In some embodiments, a second flexible member connects a second set of the plurality of attachment members. The first set of the plurality of attachment members is aligned with the second set of the plurality of attachment members such that a distance between the first flexible member and the second flexible member is greater at a first half of the carrier member than at a second half of the carrier member, the second half positioned between the first half and the bone engaging member.

According to various embodiments of the subject disclosure, a method for fixating connective tissue to bone is provided. The method comprises engaging connective tissue of an animal with a plurality of attachment members extending from a carrier member. The method also comprises attaching a bone engaging member extending from the carrier member to a bone of the animal. In some embodiments, when the plurality of attachment members is engaged with the connective tissue and the bone engaging member is attached to the bone, the connective tissue and the bone are limited in being pulled apart from one another during physiological use of the connective tissue.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE SEVERAL VIEWS OF THE DRAWINGS

The accompanying drawings, which are included to provide further understanding of the invention and are incorporated in and constitute a part of this specification, illustrate aspects of the invention and together with the description serve to explain the principles of the invention.

FIG. 2A illustrates a side view of an attachment member and FIG. 2B illustrates a front view of the attachment member, in accordance with various embodiments of the subject disclosure.

FIGS. 3A, 3B, and 3C illustrate examples of an attachment member, in accordance with various embodiments of the subject disclosure.

FIGS. 6A, 6B, 6C, 6D, 6E, 6F, 6G, and 6H illustrate examples of various configurations of the flexible device, in accordance with various embodiments of the subject disclosure.

FIG. 7 illustrates an example of a method for fixating connective tissue, in accordance with various embodiments of the subject disclosure.

FIG. 9 illustrates an example of a method for fixating connective tissue, in accordance with various embodiments of the subject disclosure.

FIGS. 10A, 10B, 10C, and 10D illustrate an example of a method for fixating connective tissue, in accordance with various embodiments of the subject disclosure.

FIGS. 14A, 14B, 14C, 14D, 14E, 14F, 14G, and 14H illustrate examples of an attachment member coupled to a stabilizing member, in accordance with various embodiments of the subject disclosure.

FIGS. 16B and 16C illustrate examples of an adjustment member, in accordance with various embodiments of the subject disclosure.

FIG. 18A illustrates an example of connective tissue and a bone prior to being fixated to one another, in accordance with various embodiments of the subject disclosure.

FIG. 18B illustrates an example of the connective tissue and the bone being fixated to one another using a fixation device, in accordance with various embodiments of the subject disclosure.

DETAILED DESCRIPTION OF THE INVENTION

Figure 1:
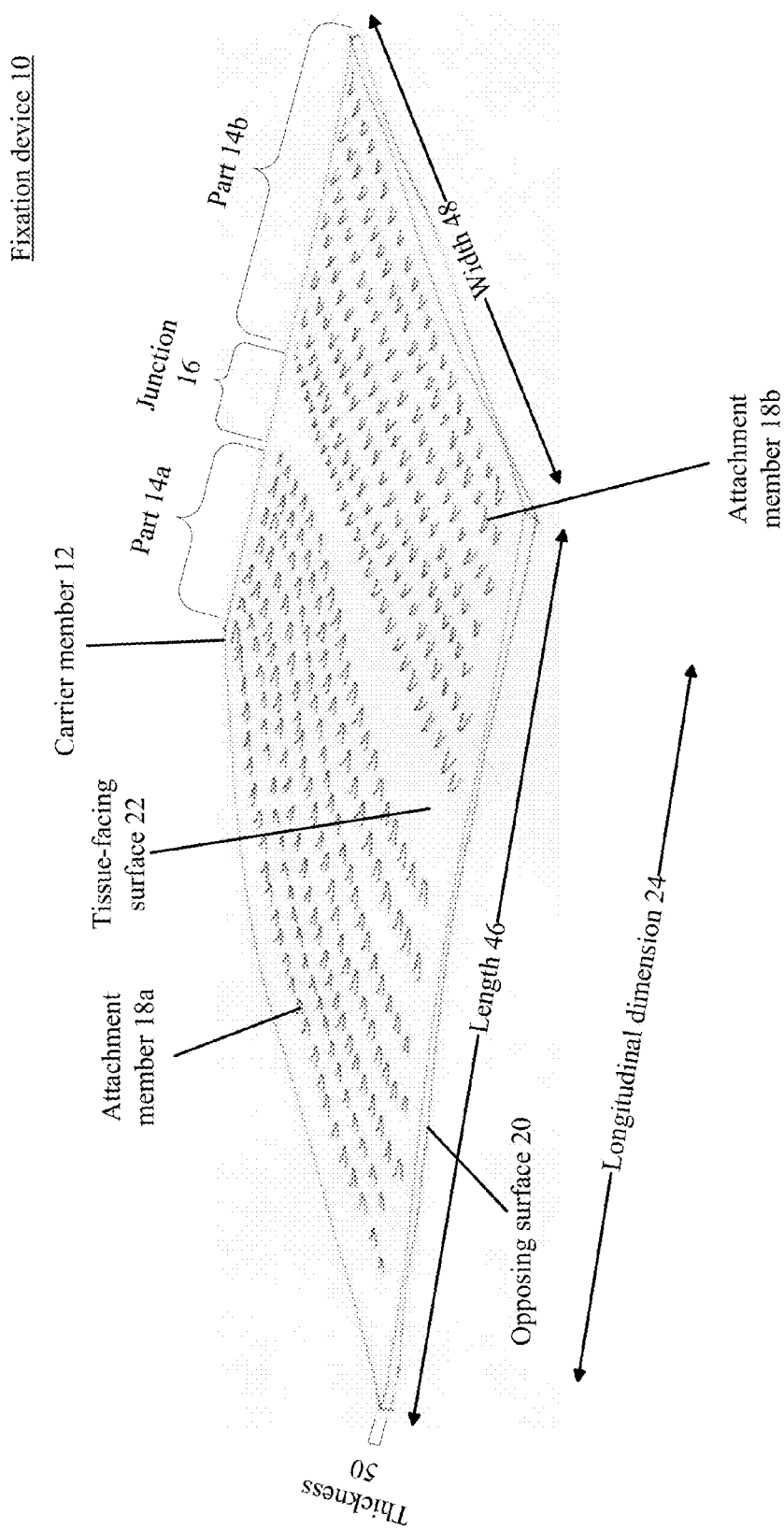
FIG. 1 illustrates an example of a fixation device for fixating connective tissue, in accordance with various embodiments of the subject disclosure.

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Immediate causes of repair failure may be attributed to failure at the tendon-suture interface. A significant limitation of suture repair is that the strength of repair may be dependent on the ability of the tendon to hold the suture. The few points at which the suture is anchored in the tendon may result in points of high stress during tensile loading, leading to shredding at the tendon-suture interface as the suture begins cutting down the tendon. Macroscopically, this is observed by the occurrence of gapping between the mended tendon ends as the anchor points in the tendon are compromised. Furthermore, trumpeting at the repair site may cause fusiform swelling in the tendon at the repair site, which may inhibit gliding. Additionally, lack of motion after repair to protect the repair may cause adhesion to the tendon sheath.

Various approaches for the improvement of tendon repair include using stronger suture materials, strengthening the tissue at the tendon-suture interface, and tissue engineering approaches in conjunction with a suture-repair. However, these approaches fail to address the issue where repair with suture may create high stress points at the few anchor points of the suture in the tendon, leading to the complications that can result in repair failure. Along with biomechanical complications associated with suture repair, the quality of the repair itself may be highly dependent on surgeon experience and skill level. The complexities of the suture techniques are technically demanding, and variations between repair quality and overall surgery length can lead to deviations between patient outcomes.

According to certain embodiments of the subject disclosure, a significant contribution to the advancement of orthopedic technologies is provided to facilitate tissue fixation, stabilization and healing, and hence, repair and restoration of function. A problem associated with suture-repair occurs when tensile loads are concentrated to a few anchor points, which may result in failure at the tendon-suture interface and ultimately repair failure. In certain embodiments, this problem associated with suture-repair is addressed. In certain embodiments, by providing a device-based approach to tendon repair, variability and quality of repair due to surgeon experience can be reduced or eliminated because of a standardized approach. In some embodiments, a device, for example with a sheath design, is provided that may limit trumpeting by investing the tendon ends. The device may also address adhesion formation by acting as a physical barrier to adhesion formation, with an outer surface coated with suitable materials to prevent adhesion. In addition to tendons, the subject technology may be applied to ligaments and other suitable tissue known to those of ordinary skill in the art.

FIG. 1 illustrates an example of a fixation device 10 for fixating connective tissue, in accordance with various embodiments of the subject disclosure. Fixation device 10 comprises a carrier member 12 having a first part 14a, a second part 14b, and a junction 16 therebetween. The carrier member 12 may be configured to encompass, at least in part, an interior space. For example, one side of the carrier member 12 may be wrapped to another side of the carrier member 12 to encompass, at least in part, the interior space. However, the two sides of the carrier member 12 do not necessarily have to be coupled to one another to encompass the interior space. The junction 16 can be a line, zone, or region. Fixation device 10 also comprises one or more first attachment members 18a protruding into the interior space and at a first angle from the first part 14a toward the junction 16. The one or more first attachment members 18a are configured to engage a first portion of connective tissue of a mammal in the interior space for attaching the first part 14a to the first portion of connective tissue. Fixation device 10 also comprises one or more second attachment members protruding from the second part into the interior space, the one or more second attachment members 18b configured to engage a second portion of connective tissue in the interior space for attaching the second part 14b to the second portion of connective tissue. When the first part 14a is attached to the first portion of connective tissue and the second part 14b is attached to the second portion of connective tissue, the first portion of connective tissue and the second portion of connective tissue are limited in being pulled apart from one another during physiological use of the connective tissue. In some embodiments, physiological use means ordinary or typical use of connective tissue in its ordinary function. For example, physiological use of ligaments and tendons in the foot, ankle, or leg may include walking, running, and jumping.

In some embodiments, carrier member 12 may have a tissue-facing surface 22, upon which the attachment members 18 (e.g., attachment members 18a and 18b) protrude from. Carrier member 12 may also have an opposing surface 20 that is opposite the side of the tissue-facing surface 22. For example, the opposing surface 20 may be a surface that faces away from the connective tissue that the fixation device 10 is affixed to. The attachment members 18 may be oriented such that they protrude towards the junction 16 and are substantially aligned with a longitudinal dimension 24 of the carrier member 12. In some embodiments, the one or more second attachment members 18b protrude at a second angle from the second part 14b toward the junction 16. In some embodiments, the carrier member 12 comprises a sheet. In some embodiments, sheet, as used herein, may be given its broadest reasonable meaning. In some embodiments, a sheet may be substantially broad, flexible, and flat. In some embodiments, the carrier member 12 comprising a sheet may refer to the carrier member 12 having a length 46, width 48 and thickness 50, where the length 46 and width 48 each are at least two times, three times, four times, five times, eight times, ten times, 15 times, 20 times, 25 times, 50 times, 100 times, or 200 times greater than the thickness 50. In some embodiments, the carrier member 12 is substantially flat. In some embodiments, the carrier member 12 is integral with the attachment members 18. In some embodiments, the longitudinal dimension 24 of the carrier member 12 may be the direction connecting the first part 14a and the second part 14b (e.g., a direction substantially perpendicular to the junction and substantially in the plane of the carrier member 12).

In some embodiments, fixation device 10 may comprise biomaterial and can be formed either prior to or upon tissue placement into a tissue joining cuff that exerts holding forces on connective tissue, comparable to a suture repair, without the destructive effects mentioned previously. In some embodiments, the attachment members 18 can be rigid and produce a porcupine-quill (or alligator teeth) mimetic securing effect by resisting tissue pull-out. The attachment members 18 may spread the tensile loading forces among many points, so as not to overload the connective tissue at any single anchor point, reducing tissue trauma and increasing immobilizing forces within the fixation device 10. Furthermore, the orientation of the attachment members 18a and the attachment members 18b allow for easy insertion of connective tissue into the cuff one way, but restrict removal or movement in the opposite direction, similar to how a finger can slide into a Chinese finger-trap but not pull out. When the fixation device 10 is attached to portions of connective tissue, the portions of connective tissue are limited in being pulled apart from one another for facilitating repair and re-union of the connective tissue within fixation device 10.

FIG. 2A illustrates a side view of an attachment member 18 and FIG. 2B illustrates a front view of the attachment member 18, in accordance with various embodiments of the subject disclosure. The attachment member 18 and the carrier member 12 meet at a base 36. The attachment member 18 comprises a body 26, a tip 34, and a base center 38. In some embodiments, the body 26 may be the portion of the attachment member 18 that protrudes from the carrier member 12. As shown in FIG. 2A, an attachment member 18 may protrude from the carrier member 12 at an angle 26. In some embodiments, the angle 26 is measured according to techniques known to those of ordinary skill in the art. In some embodiments, the angle 26 is measured between the tissue-facing surface 22 of the carrier member 12 and a line connecting the tip 34 and the base center 38. In some embodiments, angle 26 is less than or equal to about 5 degrees, 10 degrees, 15 degrees, 20 degrees, 30 degrees, 40 degrees, 45 degrees, 50 degrees, 65 degrees, 75 degrees, or 85 degrees. In some embodiments, the angle 26 of an attachment member 18a protruding from part 14a may be of the same magnitude as the angle 26 of an attachment member 18b protruding from part 14b.

According to certain embodiments, the average thickness 28 of an attachment member 18 may be measured along a direction substantially parallel to a longitudinal dimension 24 of the carrier member 12. In some embodiments, the average thickness 28 of an attachment member 18 is such that when a part 14 of carrier member 12 is attached to a portion of connective tissue, angle 26 is maintained at less than about 5 degrees, 10 degrees, 15 degrees, 20 degrees, 30 degrees, 40 degrees, 45 degrees, 50 degrees, 65 degrees, 75 degrees, 85 degrees, or 90 degrees during physiological use of the connective tissue.

In some embodiments, a height 32 of an attachment member 18 is measured from the carrier member 12 to the farthest most extent that the attachment member 18 protrudes from the carrier member 12 (e.g., at the tip 34). In some embodiments, the average height of an attachment member 18 is greater than about 6 millimeters, between about 6 and 4 millimeters, between about 4 millimeters and 2 millimeters, between about 2 millimeters and 1.75 millimeters, between about 1.75 millimeters and 1.50 millimeters, between about 1.50 millimeters and about 1.25 millimeters, between about 1.25 millimeters and about 1 millimeter, between about 1 millimeter and about 0.75 millimeter, between about 0.75 millimeter and about 0.5 millimeter, between about 0.5 millimeter and about 0.25 millimeter, between about 0.25 millimeter and about 0.10 millimeter, between about 0.10 millimeter and about 0.075 millimeter, between about 0.075 millimeter and about 0.05 millimeter, between about 0.05 millimeter and about 0.025 millimeter, between about 0.025 millimeter and about 0.01 millimeter, or less than about 0.01 millimeter.

In some embodiments, the greatest width 30 of a base 36 of an attachment member 18 is measured along a direction substantially perpendicular to a longitudinal dimension of the base 36 and substantially parallel to the tissue-facing surface 22, the longitudinal dimension of the base 36 being a direction the attachment member 18 is protruding toward in substantially the same plane as the base 36. In some embodiments, the longitudinal dimension of the base 36 is the same as the longitudinal dimension 24 of carrier member 12. In some embodiments, a ratio of a greatest width 30 of a base 36 of an attachment member 18 to an average height of the attachment member 18 is greater than or equal to about 1.4, between about 1.4 and 1.2, between about 1.2 and 1.0, between about 1.0 and 0.95, between about 0.95 and about 0.90, between about 0.90 and about 0.80, between about 0.80 and about 0.70, between about 0.70 and about 0.60, between about 0.60 and about 0.50, between about 0.50 and about 0.40, between about 0.40 and about 0.30, between about 0.30 and about 0.20, between about 0.20 and about 0.10, or less than or equal to about 0.05.

According to various embodiments, the attachment member 18 is configured such that at least about 25%, 50%, 75%, or 95% of the body 26 of the attachment member 18 penetrates a portion of intended connective tissue when a part 14 of the carrier member 12 is attached to the portion of connective tissue. In some embodiments, the attachment member 18 is configured to penetrate the portion of intended connective tissue at a depth of less than about 0.01 millimeter, between about 0.01 millimeter and about 0.025 millimeter, between about 0.025 millimeter and about 0.05 millimeter, between about 0.05 millimeter and about 0.075 millimeter, between about 0.075 millimeter and about 0.10 millimeter, between about 0.10 millimeter and about 0.25 millimeter, between about 0.25 millimeter and about 0.50 millimeter, between about 0.50 millimeter and about 0.75 millimeter, between about 0.75 millimeter and about 1 millimeter, between about 1 millimeter and about 1.25 millimeters, between about 1.25 millimeters and about 1.50 millimeters, between about 1.50 millimeters and about 1.75 millimeters, between about 1.75 millimeters and about 2 millimeters, between about 2 millimeters and about 3 millimeters, between about 3 millimeters and about 4 millimeters, between about 4 millimeters and about 6 millimeters, or greater than about 6 millimeters. The amount of penetration may depend on the force applied to the attachment member 18, the density of the intended connective tissue, the hardness of the connective tissue and/or the attachment member 18, or other suitable factors known to those of ordinary skill in the art.

A plurality of attachment members 18 may protrude from a part 14 of a carrier member 12. The part 14 may comprise a tissue-facing surface 22 that faces the connective tissue when the part 14 engages a first portion of the connective tissue. A fixation device 10 may comprise a number of different densities of attachment members 18 on the part 14. For example, the part 14 and each of the plurality of the attachment members 18 may meet at a respective base 36 having an area. A ratio of the total area of all the bases 36 to the total area of the tissue-facing surface 22 of the part 14 may be greater than or equal to about 0.05, 0.10, 0.20, 0.30, 0.40, 0.50, 0.60, 0.70, 0.80, 0.90, or 0.95. In some embodiments, a high ratio is desirable. In some embodiments, by having a large number of attachment members 18 disposed on a carrier member 12, the resulting surface disperses load over a larger surface area as opposed to a carrier member 12 with fewer attachment members 18.

FIGS. 3A, 3B, and 3C illustrate examples of an attachment member 18, in accordance with various embodiments of the subject disclosure. An attachment member 18 may have a different shape or angle with respect to other attachment members 18 protruding from the same carrier member 12. In some embodiments, all the attachment members 18 protruding from a part 14 of a carrier member 12 may be oriented in the same direction. In some embodiments, an attachment member 18 may comprise at least one of a hook, a barb, and a pin.

In some embodiments, a method for creating oriented, spaced attachment members 18 in carrier member 12 uses an oriented direct fiber transfer process to embed oriented fibers of attachment members 18 into carrier member 12 by either electrostatic forces or mechanical alignment to yield the final device.

In some embodiments, an electrostatic process utilizes a field of static electricity to orient the fibers of attachment members 18 relative to the applied electrostatic field and promote a perpendicular alignment of the fibers with respect to carrier member 12. For example, uncured carrier member 12 resin in a mold can be passed between the potentials of a high voltage electrostatic field. A local electrode may be utilized to give the fiber an electrostatic charge. The charged fibers may become aligned with the electrical field lines of force. The carrier member 12 resin and/or the grounded parts of the application machine may form a ground potential. The fibers of attachment members 18 may therefore be electrostatically attracted toward the carrier member 12 in the mold in the presence of the field, where they become embedded in the uncured liquid resin of carrier member 12 in its mold prior to curing. With this process, most fibers may be embedded within the carrier member 12 resin surface, adhering to the resin and may be oriented relative to carrier member 12 dictated by the orientation of the electrostatic field and electrodes placing the fibers relative to the plane of carrier member 12.

In some embodiments, the attachment members 18 may be non-conductive or uncharged, and the attachment members 18, as short fibers, may be transported and aligned predominately perpendicular to the release sheet through mechanical means, such as a sieving screening or alignment mask through which the attachment members 18 may fall through the openings to align and orient at fixed positions and at defined spacings in the resin prior to thermal or photo-curing.

In some embodiments, attachment members 18 embedded into carrier member 12 can include natural or synthetic fibers such as rayon, and other types of conductive materials including nylon, polyamide, polyester and similar synthetic fibers. The attachment members 18 can also include pre-formed ceramic or metal fibers, or related large aspect ratio needles, of millimeter length dimensions. In some embodiments, all of the attachment members 18 may be embedded into the carrier member 12 at a defined spacing and angular orientation relative to the plane of carrier member 12, and subsequently cured in place by thermal or photonic means securely to prevent release under stress or strain.

Figure 4A:
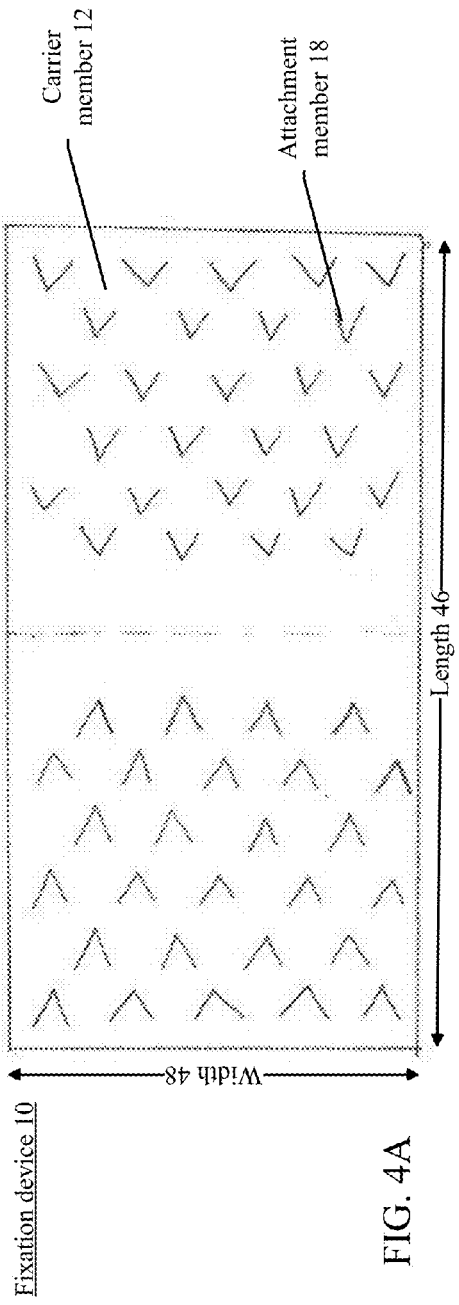
FIGS. 4A and 4B illustrate arrangements of the attachment members, in accordance with various embodiments of the subject disclosure.
Figure 4B:
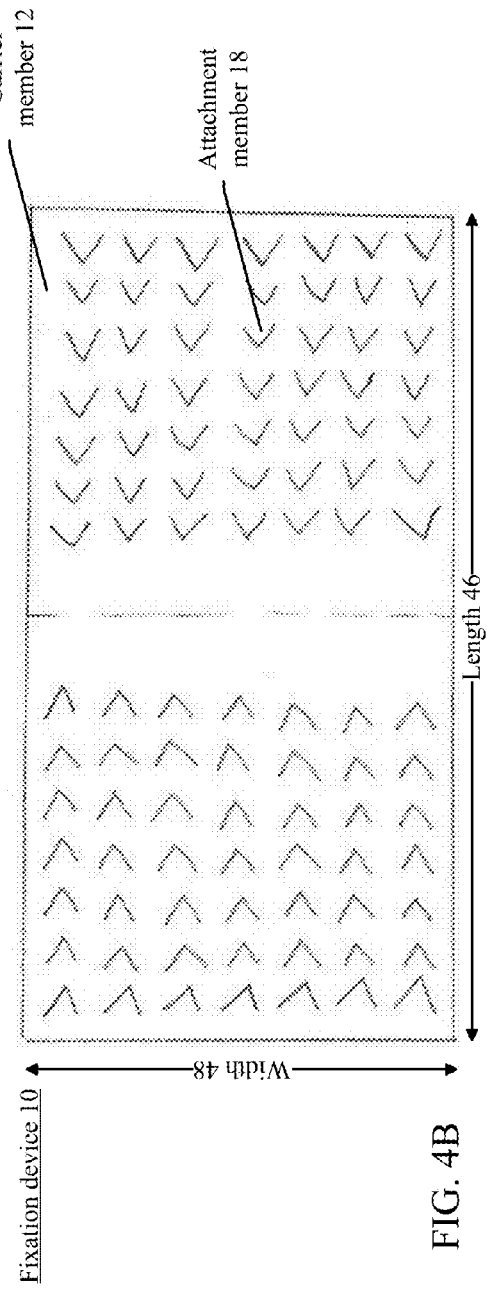

FIGS. 4A and 4B illustrate arrangements of the attachment members 18, in accordance with various embodiments of the subject disclosure. In some embodiments, attachment members 18 protruding from a carrier member 12 may be arranged in various configurations or in random configurations. As shown in FIG. 4A, the attachment members 18 are arranged with respect to the carrier member 12 in a staggered array. As shown in FIG. 4B, the attachment members 18 are arranged with respect to the carrier member 12 in a grid-like array. The attachment members 18 may be arranged with respect to the carrier member 12 in at least one of the grid-like array and the staggered array.

Figure 5A:
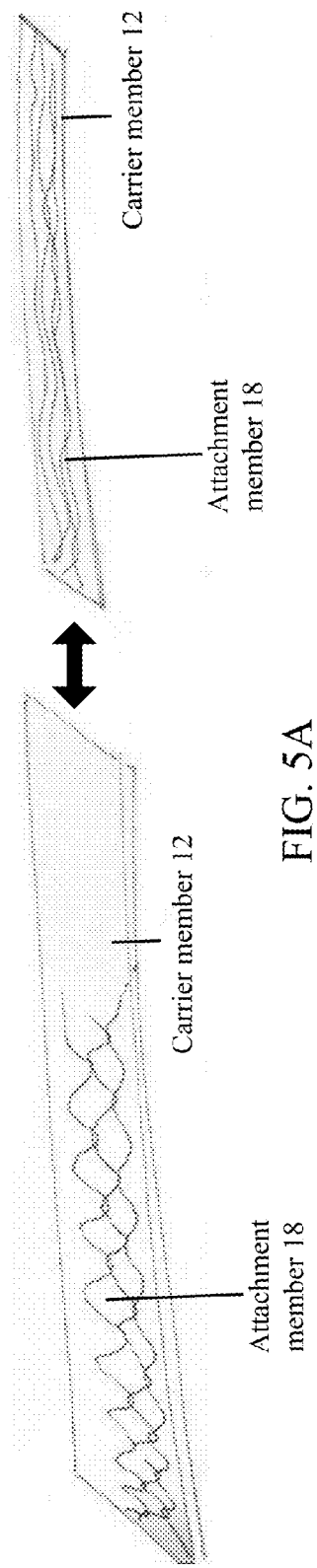
FIGS. 5A and 5B illustrate the flexibility of the fixation device, in accordance with various embodiments of the subject disclosure.
Figure 5B:
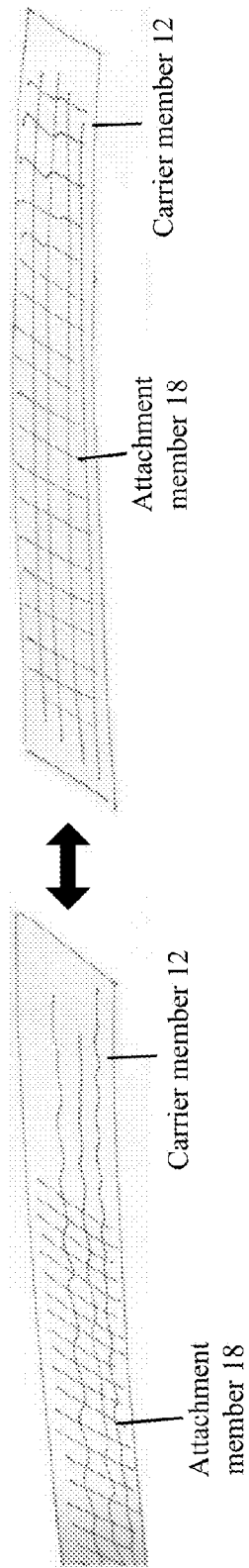

FIGS. 5A and 5B illustrate the flexibility of the fixation device 10, in accordance with various embodiments of the subject disclosure. In some embodiments, the fixation device 10 is elastic. For example, FIGS. 5A and 5B illustrate that the fixation device 10 can be stretched in its longitudinal direction. In some embodiments, the carrier member 12 may be flexible such that the carrier member 12 can readily conform to the connective tissue. In some embodiments, an attachment member 18 protruding from the carrier member 12 is less elastic than is the carrier member 12. In some embodiments, the carrier member 12 allows deployment of the attachment members 18 into a fully extended and exposed position for optimal tissue engagement by stretching the carrier member 12.

Figure 6C:
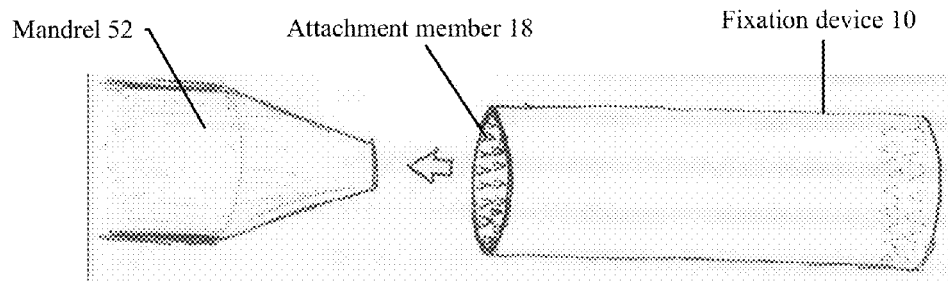

FIGS. 6A, 6B, 6C, 6D, 6E, 6F, 6G, and 6H illustrate examples of various configurations of the flexible device 10, in accordance with various embodiments of the subject disclosure. As shown in FIG. 6A, the fixation device 10 may be conformed about its longitudinal dimension 24 into a cylindrical structure such that the attachment members 18 are in an interior of the fixation device 10. Thus, the opposing surface 20 is on an exterior of the fixation device 10. This configuration may be used, for example, to wrap the fixation device 10 around portions of connective tissue. As shown in FIG. 6B, the fixation device 10 may be conformed about its longitudinal dimension 24 into a cylindrical structure such that the attachment members 18 are in an exterior of the fixation device 10. Thus, the opposing surface 20 is in an interior of the fixation device 10. This configuration may be used, for example, to place the fixation device 10 within various organs and tissue as a stent-like device. In some embodiments, the fixation device 10 may be used as a tape-like or bandage-like device and placed over tears or rips in tissue or organs to facilitate repair. In some embodiments, two fixation devices 10 may be placed on opposite sides of a tissue site to be fixed. The attachment members 18 from each face of the two fixation devices 10 may be engaged into opposite faces of the tissue to be fixed, and the edges of two fixation devices 10 may be secured to each other around the tissue site to hold the tissue within a sandwich structure between the two fixation devices 10.

In some embodiments, at least one of the carrier member 12 and the attachment members 18 may comprise a shape memory material. In this case, the fixation device 10 may spontaneously conform to a shape of the connective tissue upon application of a stimulus (e.g., light (ultraviolet or other forms), heat, moisture (e.g., aqueous moisture), and/or other suitable stimuli). In some embodiments, the stimulus may comprise at least one of light, heat, and organic solvents. For example, the fixation device 10 may deploy and roll up around connective tissue to engage the connective tissue upon application of the stimulus. In some embodiments, the fixation device 10 may be in a flat configuration when engaging the connective tissue. The fixation device 10 may then conform to the connective tissue (e.g., wrap around the connective tissue) upon application of the stimulus. In some embodiments, the attachment members 18 may be deployed based on the shape memory material. In some embodiments, the attachment members 18 may be configured to transform from a non-engaging configuration to an engaging configuration upon application of a stimulus. For example, when the stimulus has not been applied, the attachment members 18 may be in a non-engaging configuration such as being hidden, lying flat against the tissue facing surface 22, being sufficiently soft, or otherwise being in a configuration in which the attachment members 18 do not engage or minimally engage connective tissue when the fixation device 10 engages the connective tissue. Upon application of the stimulus, the attachment members 18 may transform into an engaging configuration such as becoming exposed, protruding at a suitable angle from the tissue facing surface 22, becoming sufficiently rigid, or otherwise transforming into a configuration in which the attachment members 18 may sufficiently engage connective tissue when the fixation device 10 engages the connective tissue. In one example, the attachment members 18 may be hidden when dry, but may be exposed and become rigid when wet to engage the connective tissue.

Figure 6D:
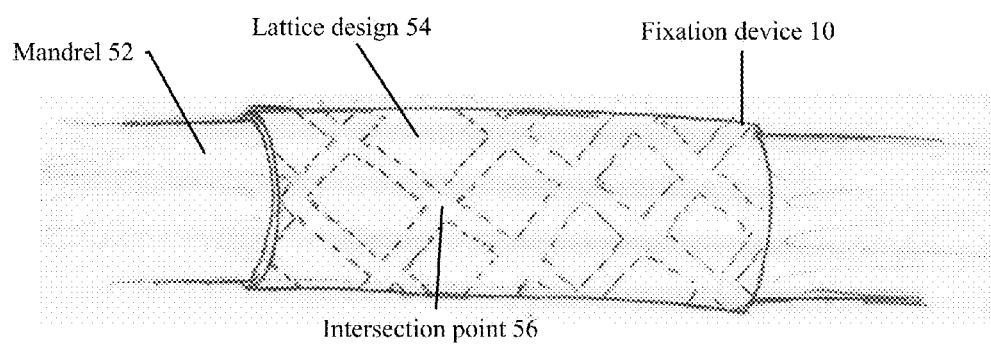
Figure 6E:
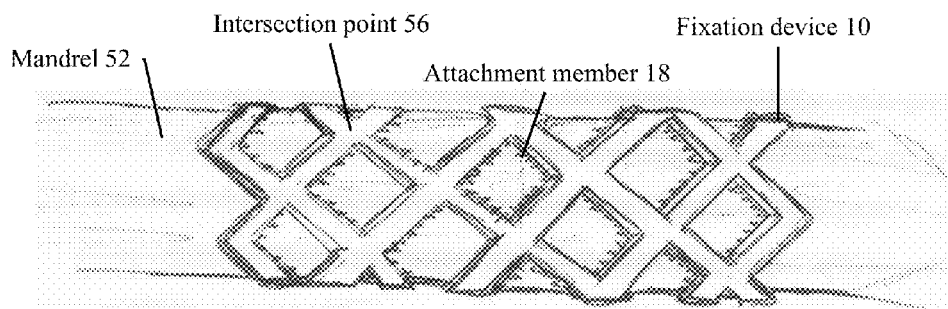

According to certain embodiments, at least part of the carrier member 12 of fixation device 10 may comprise a lattice design. As shown in FIGS. 6C and 6D, fixation device 10, which is conformed in a cylindrical structure, may be loaded onto a mandrel 52. Using laser cutting or other suitable techniques known to those of ordinary skill in the art, a lattice design 54 may be created on the carrier member 12 of fixation device 10, as shown in FIGS. 6D and 6E. Such a configuration beneficially allows for diffusion to and from the connective tissue through the holes of the lattice design 54 when the fixation device 10 is engaged to the connective tissue. In some embodiments, such a configuration may also allow fixation device 10 to be of sufficient elasticity, for example, to stretch and wrap around connective tissue. In some embodiments, the attachment members 18 may protrude from the one or more intersection points 56 of the lattice design 54. However, the attachment members 18 may protrude anywhere from the carrier member 12, including along the sides of the criss-cross pattern of the lattice design 54.

Figure 6F:
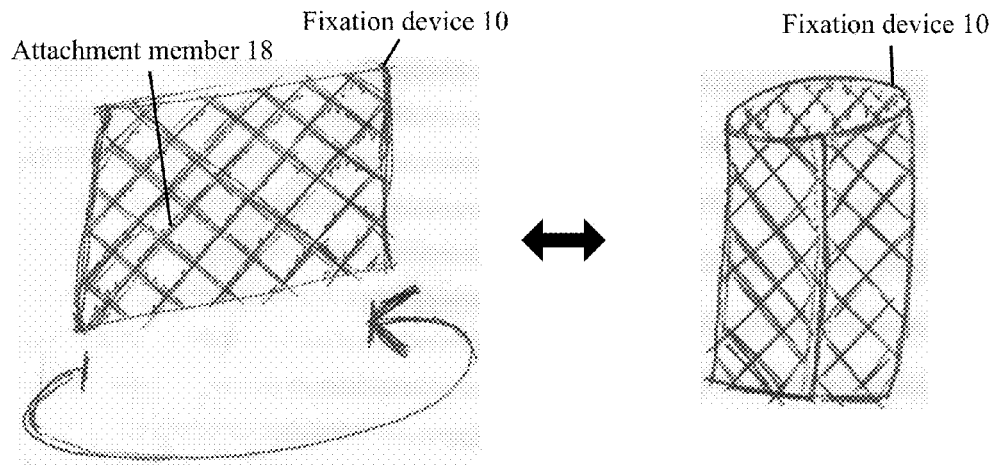
Figure 6G:
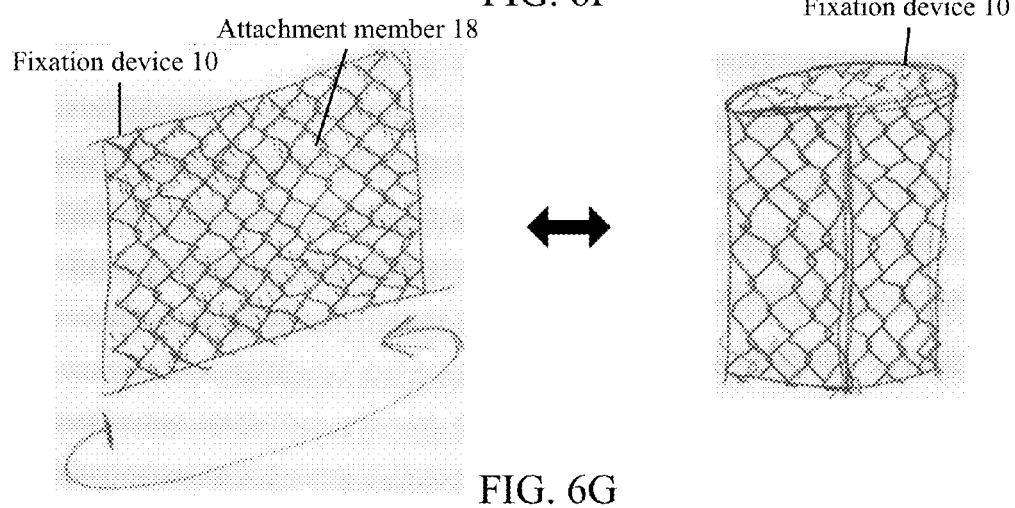
Figure 6H:
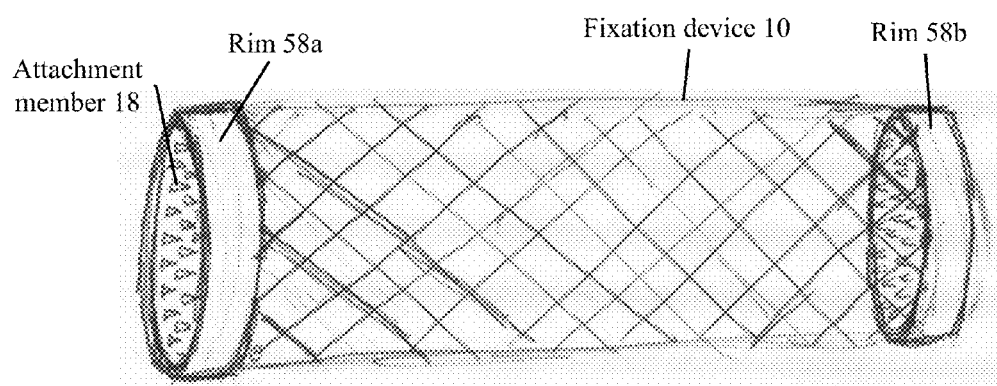

According to certain embodiments, other techniques may be used to provide a fixation device 10 having holes on the carrier member 12 to facilitate diffusion to and from the connective tissue when the fixation device 10 is engaged to the connective tissue. For example, as shown in FIG. 6F, strips of fiber may be weaved together to form a meshwork design for carrier member 12 of the fixation device 10. In another example, as shown in FIG. 6G, strips of fiber may be knitted together to form a meshwork design for the carrier member 12 of the fixation device 10. In some embodiments, biosensor drilling may be used to drill holes into the carrier member 12. FIG. 6H illustrates an example of the fixation device 10 conformed in a cylindrical structure and utilizing a meshwork design. The attachment members 18 may protrude from an interior of rims 58a and 58b formed at the respective openings of the cylindrical structure. However, the attachment members 18 may also protrude from other areas of the fixation device 10, including an exterior of rims 58a and 58b and/or along the fibers of the meshwork design. Although the carrier member is described as conforming into the cylindrical structure, it is understood that this cylindrical structure may, in some embodiments, refer to a substantially tubular structure. For example, the carrier member 12 may be configured to conform into an elongate and hollow structure.

Figure 8A:
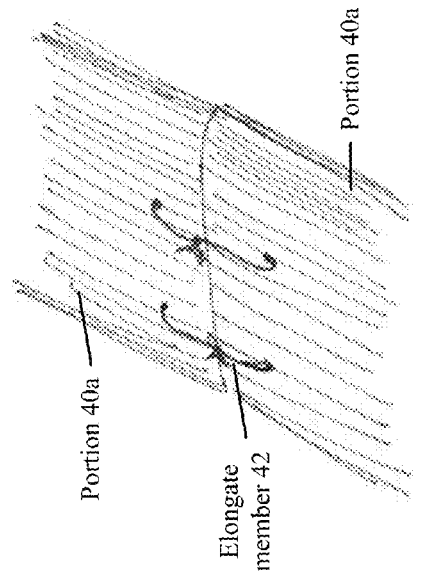
FIGS. 8A, 8B, 8C, and 8D illustrate an example of a method for fixating connective tissue, in accordance with various embodiments of the subject disclosure.
Figure 8B:
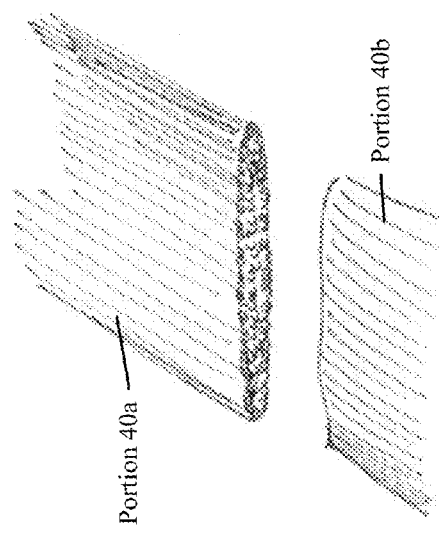
Figure 8C:
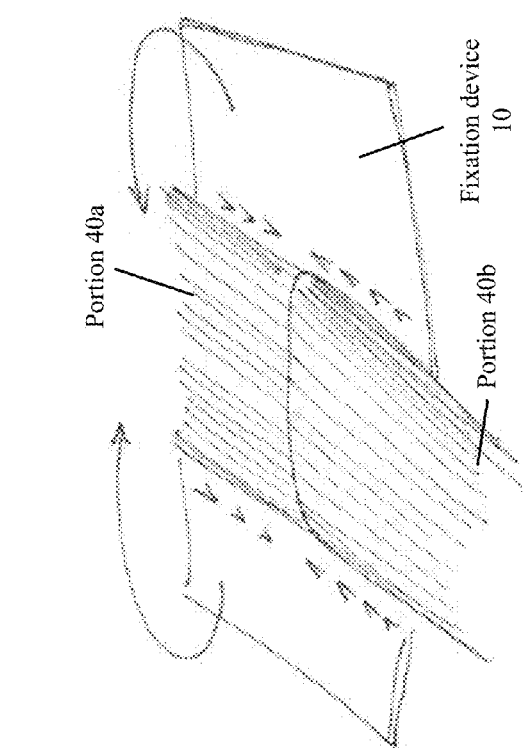
Figure 8D:
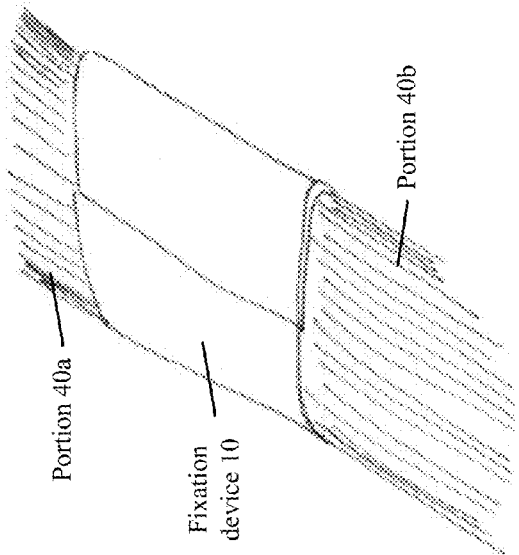
Figure 11A:
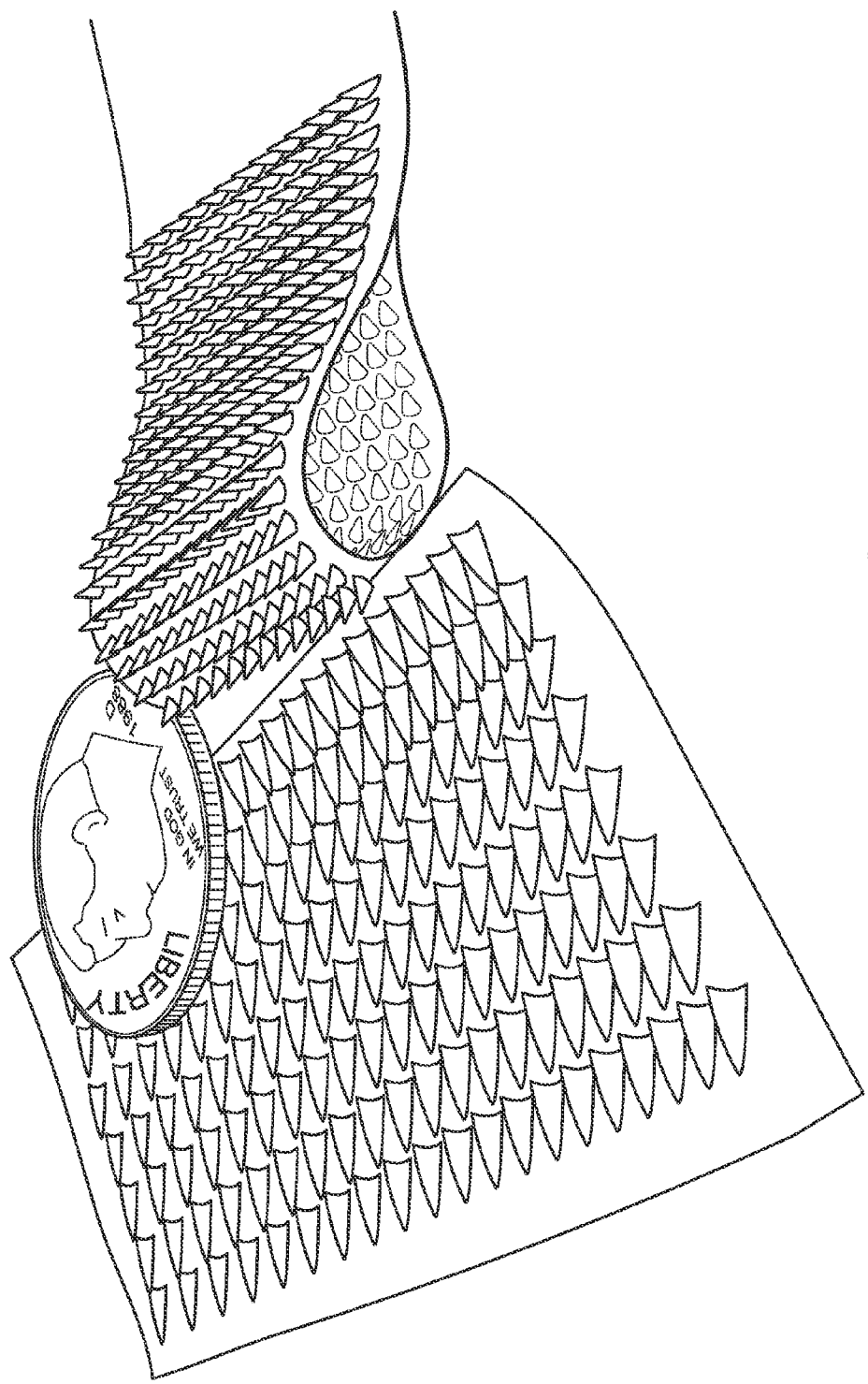
FIGS. 11A, 11B, 11C, 11D, 11E, 11F, 11G, 11H, and 11I illustrate examples of the fixation device, in accordance with various embodiments of the subject disclosure.
Figure 11B:
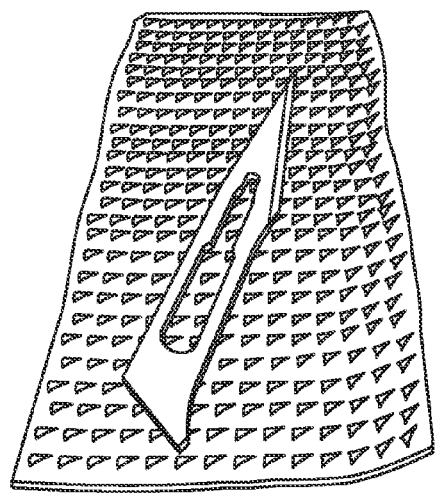
Figure 11C:
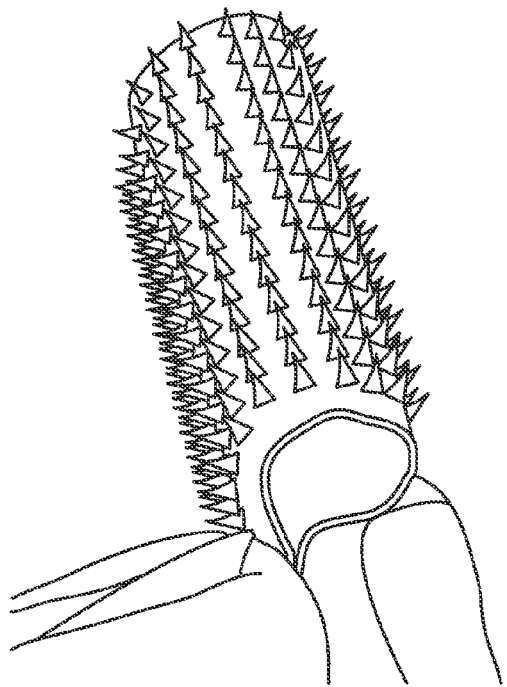
Figure 11D:
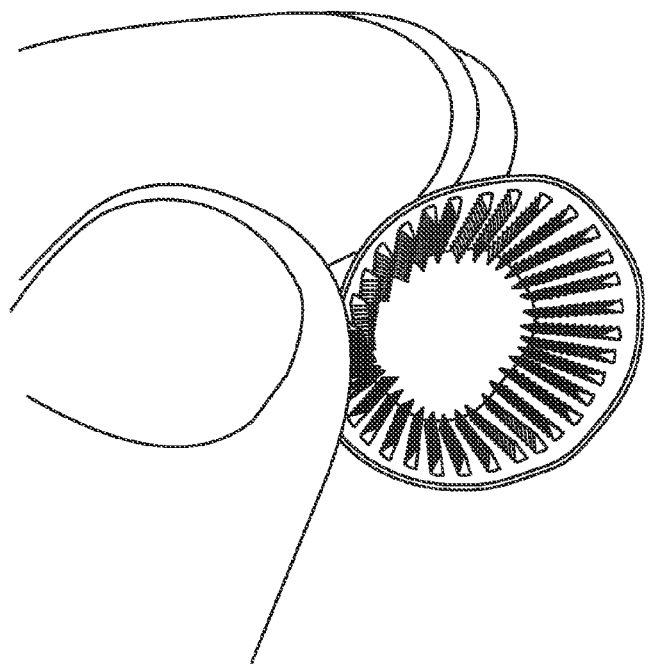
Figure 11E:
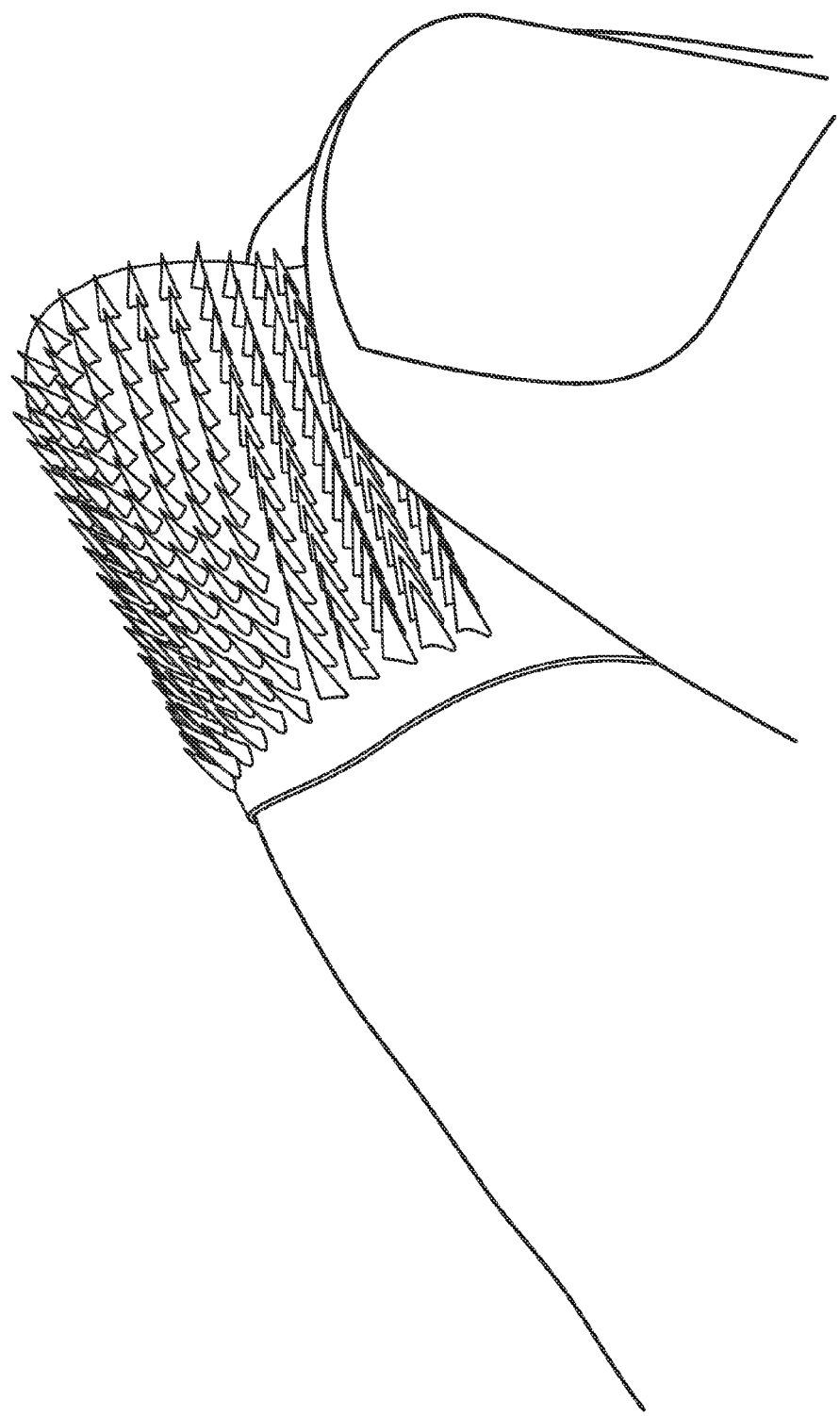
Figure 11F:
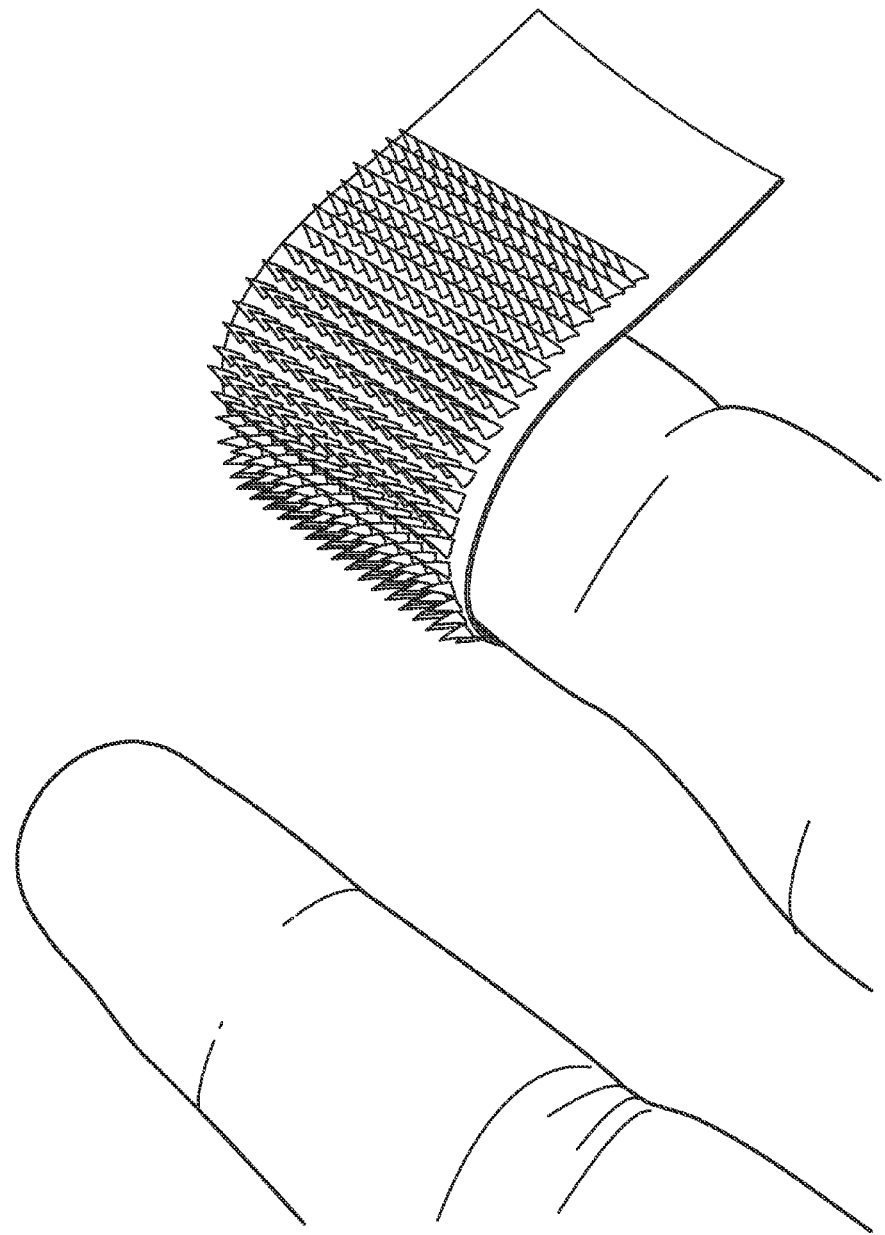
Figure 11G:
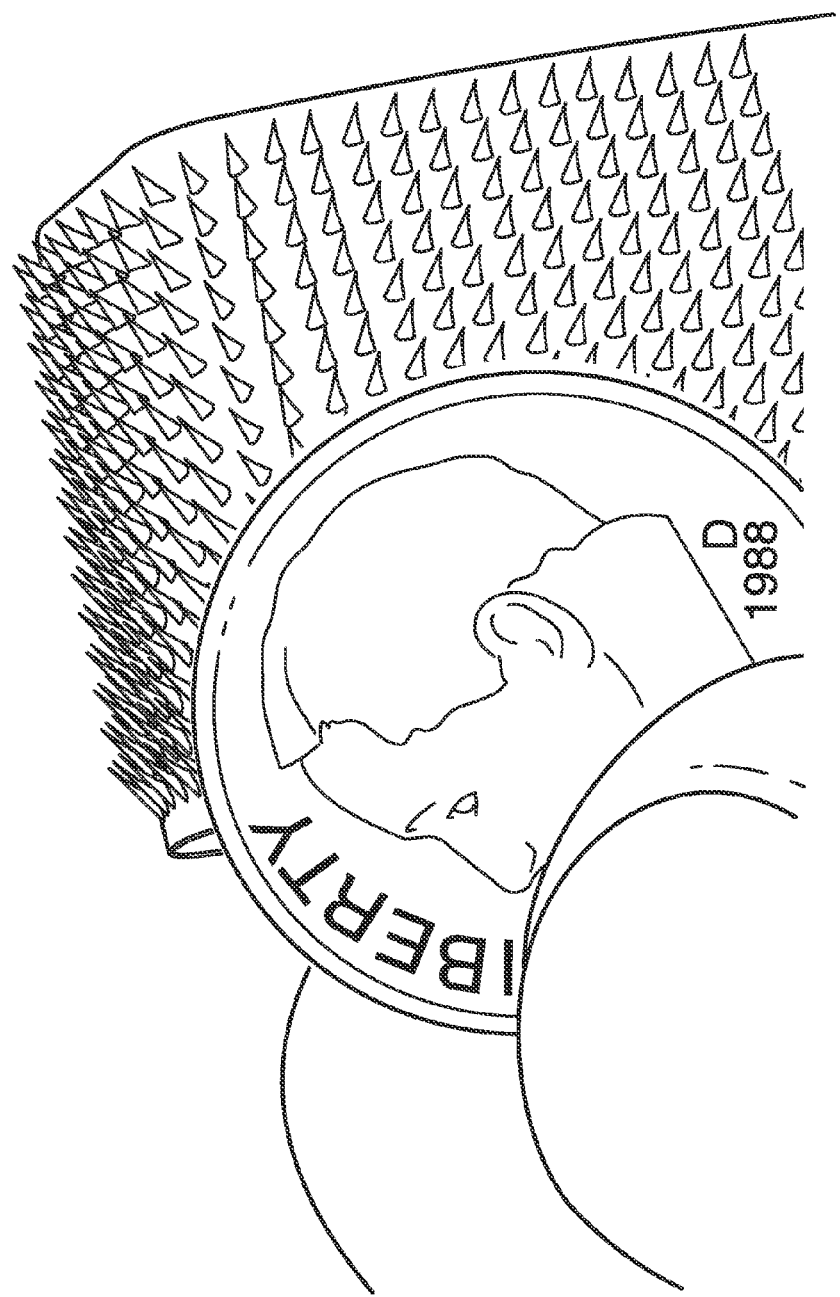
Figure 11H:
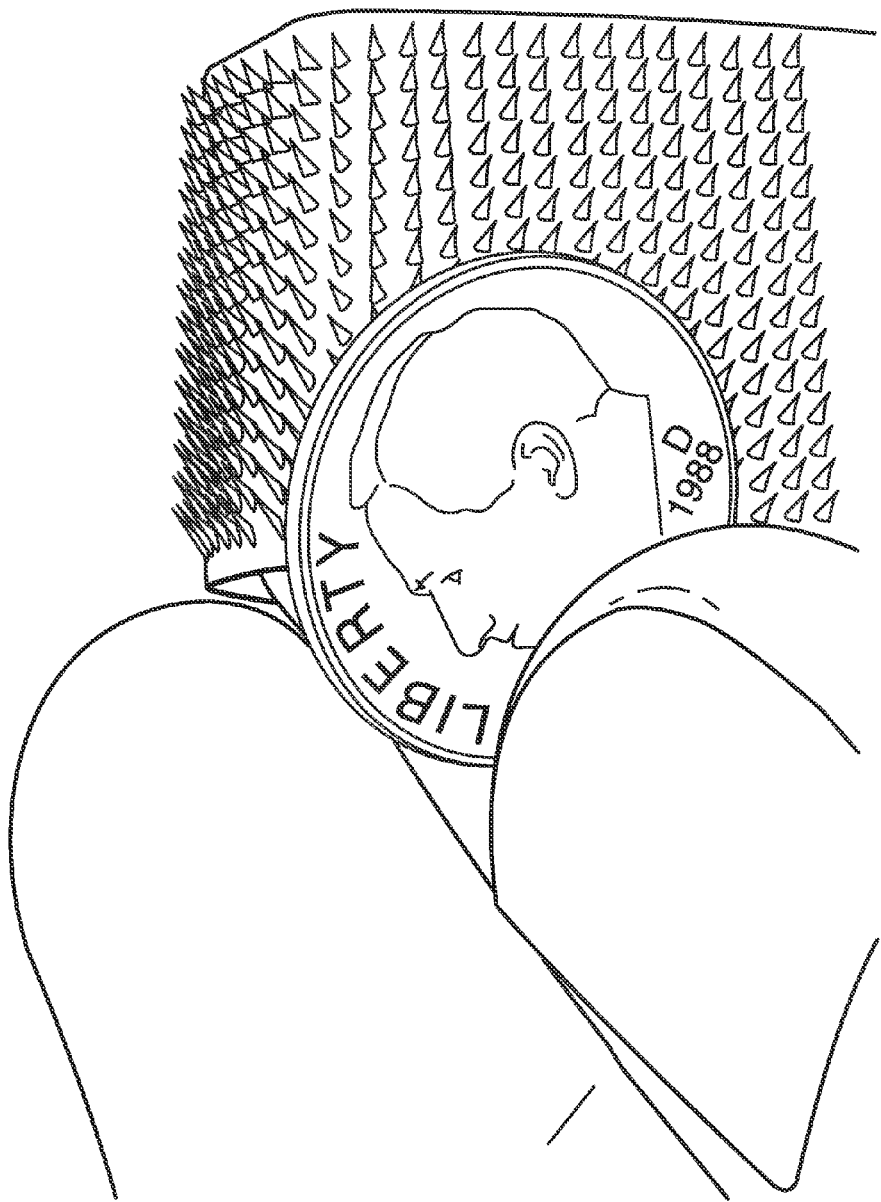
Figure 11I:
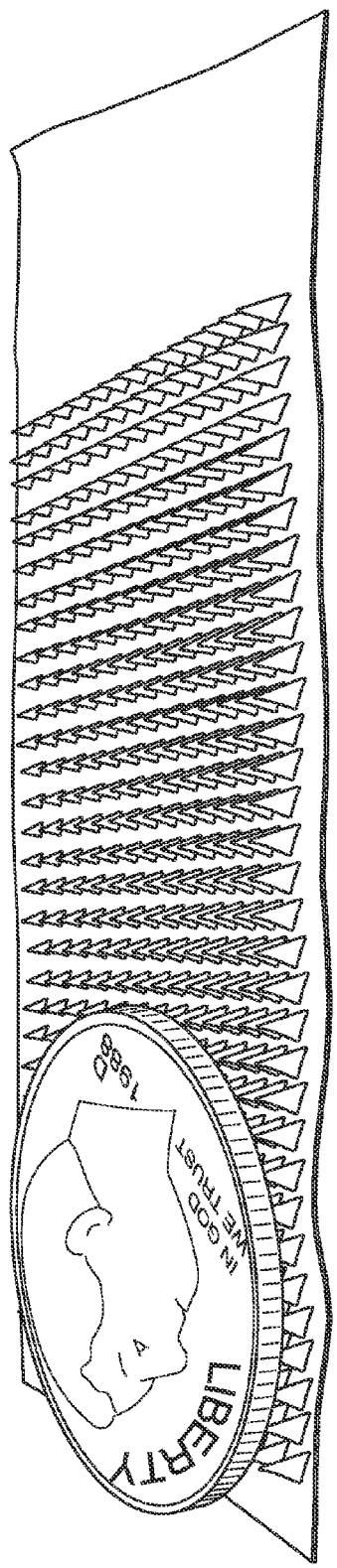

FIGS. 7, 8A, 8B, 8C, and 8D illustrate an example of a method 700 for fixating a first portion 40a of connective tissue to a second portion 40b of connective tissue, in accordance with various embodiments of the subject disclosure. Method 700 comprises affixing the fixation device 10 (e.g., as shown in FIGS. 1 and 6A) to the first portion 40a and the second portion 40b, as shown in FIGS. 8C and 8D. In some embodiments, the fixation device 10 is affixed to the first portion 40a and the second portion 40b such that (a) the first part 14a conforms to the first portion 40a and the one or more first attachment members 18a engage the first portion 40a, (b) the second part 14b conforms to the second portion 40b and the one or more second attachment members 18b engage the second portion 40b, and (c) the junction 16 is disposed approximately between the first portion 40a and the second portion 40b. In some embodiments, method 700 also comprises coupling the first portion 40a of connective tissue to the second portion 40b of connective tissue, for example, as shown in FIG. 8B with an elongate member 42. The elongate member 42 may comprise suture used to tie the first portion 40a together with the second portion 40b. The coupling may comprise other means to couple the first portion 40a to the second portion 40b. For example, the coupling may comprise attaching the first portion 40a to the second portion 40b with at least one of a suture, staple, pin, tack, surgical adhesive or glue, thermal bond, or other suitable methods known to those of ordinary skill in the art.

In some embodiments, fixation device 10 may be stretched along its longitudinal dimension 24 before being attached to the connective tissue such that when the first part 14a attaches to the first portion 40a and when the second part 14b attaches to the second portion 40b, the elasticity of the fixation device 10 causes the first part 14a attached to the first portion 40a and the second part 14b attached to the second portion 40b to be flexed back towards one another. The orientation of the one or more first attachment members 18a and the one or more second attachment members 18b may prevent the first portion 40a from being pulled apart from the second portion 40b and vice versa. In some embodiments, when the first part 14a is attached to the first portion 40a and the second part 14b is attached to the second portion 40b, the first portion 40a and the second portion 40b are limited in being pulled apart from one another during physiological use of the connective tissue.

In some embodiments, the first portion 40a comprises at least one of a ligament and a tendon. In some embodiments the second portion 40b comprises at least one of a ligament and a tendon. In some embodiments, the first portion 40a and the second portion 40b are of the same connective tissue type.

FIGS. 9, 10A, 10B, 10C, and 10D illustrate an example of a method 900 for fixating a first portion 40a of connective tissue to a second portion 40b of connective tissue, in accordance with various embodiments of the subject disclosure. Method 900 comprises providing a fixation device 10 comprising a carrier member 12 having a first part 14a, a second part 14b, and a junction 16 therebetween (e.g., as shown in FIGS. 1 and 6A). The carrier member 12 is configured to conform into a cylindrical structure (e.g., as shown in FIGS. 6A, 10B, 10C, and 10D) such that a first opening 44a is formed at the first part 14a, a second opening 44b is formed at the second part 14b, the junction 16 is disposed between the first opening 44a and the second opening 44b, the one or more first attachment members 18a protrude from the first part 14a in an interior of the cylindrical structure, and the one or more second attachment members 18b protrude from the second part 14b in the interior of the cylindrical structure. In some embodiments, method 900 comprises conforming the carrier member 12 into the cylindrical structure.

Method 900 also comprises advancing, when the carrier member 12 is conformed into the cylindrical structure, the first portion 40*a* through the first opening 44*a* into the interior of the cylindrical structure until a tip of the first portion 40*a* reaches the junction 16 such that the one or more first attachment members 18*a* engage the first portion 40*a*. In some embodiments, the advancing the first portion 40*a* comprises coupling the tip of the first portion 40*a* to a first elongate member 42*a* and advancing the first elongate member 42*a* through the first opening 44*a* into the interior of the cylindrical structure such that the first portion 40*a* is drawn into the interior of the cylindrical structure through the first opening 44*a* (e.g., as shown in FIGS. 10B and 10C). The first elongate member 42*a* may comprise suture, thread, or any other suitable mechanism known to those of ordinary skill in the art useful for pulling the first portion 40*a*.

Method 900 also comprises advancing, when the carrier member 12 is conformed into the cylindrical structure, the second portion 40*b* through the second opening 44*b* into the interior of the cylindrical structure until a tip of the second portion 40*b* reaches the junction 16 such that the one or more second attachment members 18*b* engage the second portion 40*b*. In some embodiments, the advancing the second portion 40*b* comprises coupling the tip of the second portion 40*b* to a second elongate member 42*b* and advancing the second elongate member 42*b* through the second opening 44 into the interior of the cylindrical structure such that the second portion 42*b* is drawn into the interior of the cylindrical structure through the second opening 44*b*. The second elongate member 42*b* may comprise suture, thread, or any other suitable mechanism known to those of ordinary skill in the art useful for pulling the second portion 40*b*. In some embodiments, when the first part 14*a* is attached to the first portion 40*a* and the second part 14*b* is attached to the second portion 40*b*, the first portion 40*a* and the second portion 40*b* are limited in being pulled apart from one another during physiological use of the connective tissue.

According to various embodiments of the subject disclosure, the fixation device 10 as discussed herein may be applied for use in other applications involving tissue repair. For example, in addition to use with tendons and ligaments, the fixation device 10 may be applied to the organs of the gastrointestinal system or urinary system of a mammal. These organs may include, but not limited to, the esophagus, stomach, small and large intestines, mouth, colon, anus, appendix, gallbladder, liver, pancreas, kidneys, urethers, bladder, urethra, or other suitable organs known to those of ordinary skill in the art. The fixation device 10 may be used as a cylindrical structure (e.g., as shown in either FIGS. 6A and 6B) in attaching to tissue or alternatively may be used as a tape-like, bandage-like, or sandwiching-like device to be patched onto organs where repair is needed. FIGS. 11A, 11B, 11C, 11D, 11E, 11F, 11G, 11H, and 11I illustrate examples of the fixation device 10, in accordance with various embodiments of the subject disclosure.

Figure 12B:
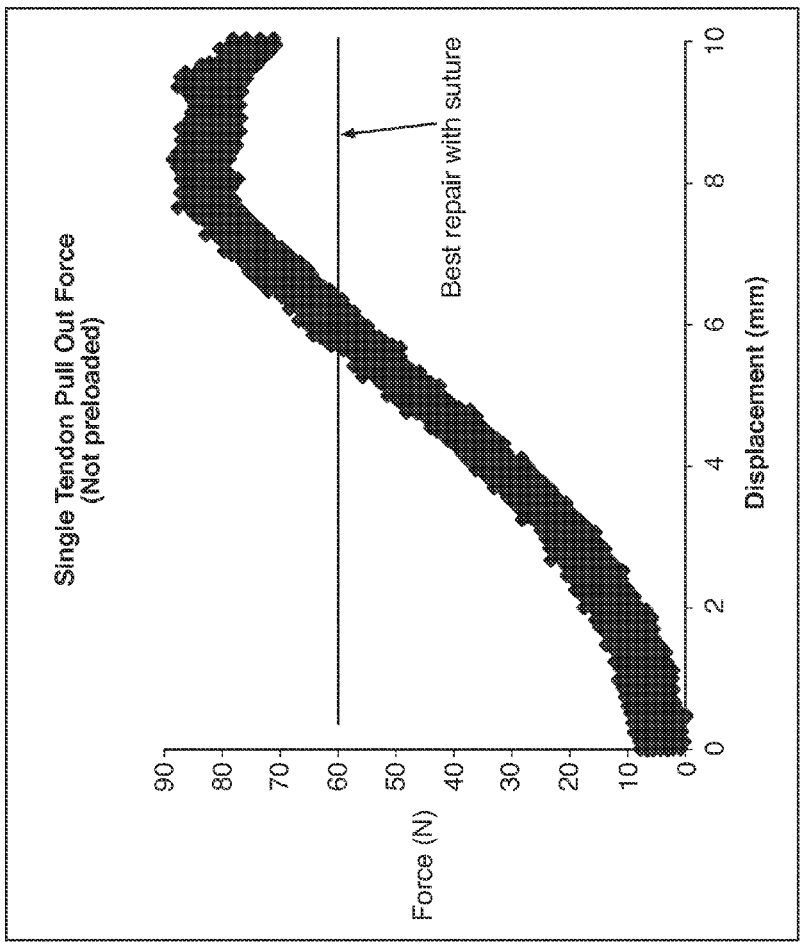
FIGS. 12A and 12B of examples of experiments conducted with the fixation device, in accordance with various embodiments of the subject disclosure.
Figure 12A:
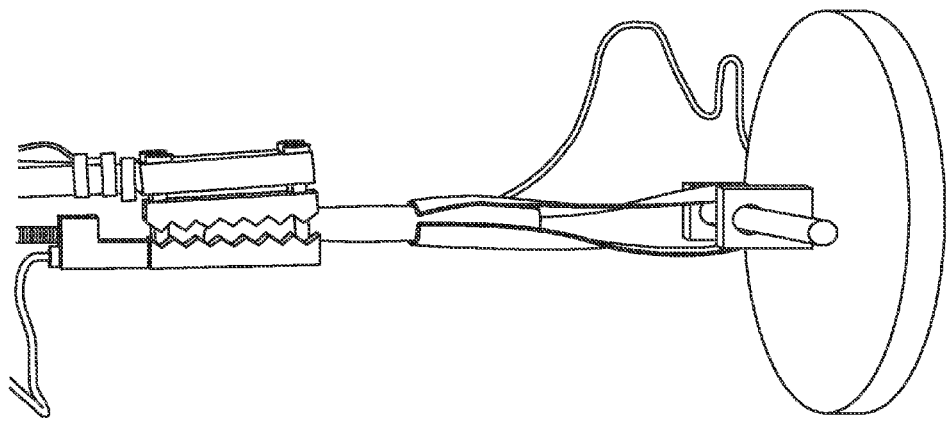

FIGS. 12A and 12B of examples of experiments conducted with the fixation device 10, in accordance with various embodiments of the subject disclosure. FIG. 12A illustrates an example of single-tendon uniaxial tensile testing to determine the holding strength of the fixation device 10 on a tendon. To test the holding strength, the force needed to pull the tendon out of the sleeve is determined by uniaxial tensile loading on an Instron at a displacement ramp rate of about 0.5 millimeters per second while recording displacement and force on the load cell. This test set-up involves wrapping the fixation device 10 around a bovine tendon to cover the area one inch up from the end of the tendon, with the attachment members 18 facing toward the end of the tendon. The fixation device 10 is taped circumferentially to prevent the device from opening up, and the two ends of a nylon strap are glued on opposite sides of the formed sleeve to form a loop. The free end of the tendon is placed into a freeze clamp, while the loop is secured to the testing bench via a bolt to hold the strap down. FIG. 12B illustrates a single tendon pull out force of the fixation device 10, in accordance with various embodiments of the subject disclosure. As shown in FIG. 12B, the strength of fixation of suture repair is at about 60 Newtons, with a failure of fixation defined as a gap of greater than 3 millimeters. In some embodiments, use of the fixation device 10 may allow for a force being applied at greater than about 60 Newtons.

Figure 13:
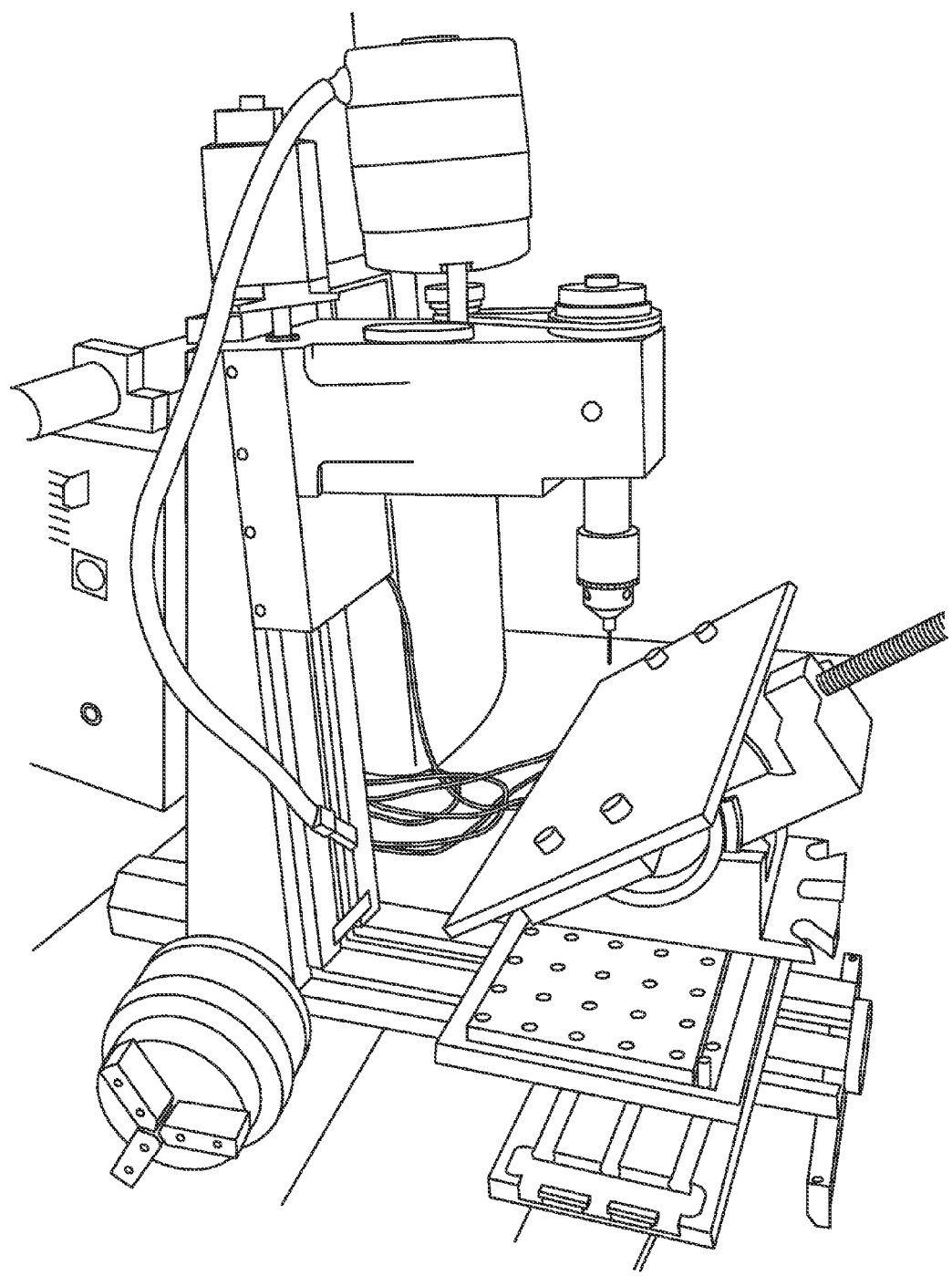
FIG. 13 illustrates an example of manufacturing the fixation device, in accordance with various embodiments of the subject disclosure.

FIG. 13 illustrates an example of manufacturing the fixation device 10, in accordance with various embodiments of the subject disclosure. As shown in FIG. 13, a computer numerical controlled (CNC) machine may be used to fabricate the fixation device 10. In some embodiments, the fixation device may be manufactured utilizing solventless fabrication techniques. To move into solvent-free production, photo-curable polymers may be used, as well as thermal-melt processing methods in place of the solvent casting techniques. This may be advantageous in a manufacturing perspective because there would be no organic waste to deal with and no additional time needed to extract residual solvent that may still be present in the materials of the fixation device 10. Because the fixation device 10 is implanted into the body of a mammal, it is important to eliminate concerns of toxicity due to possibility of residual chemicals from processing. In some embodiments, materials to be used in fabricating the fixation device 10 include materials already approved for implantation in the body by the United States Food and Drug Administration (FDA).

A CNC machine may be used to create a mold for fabricating the fixation device 10. The CNC machine tool may move a surgical blade in and out of the mold medium to create surface structures and indentations. A tilting platform on the CNC benchtop may allow its blade to enter the mold at various angles. The size of each attachment member 18 may be controlled by the depth the blade enters the mold. The angle 26 of each attachment member 18 may be controlled by the angle of the tilting platform. The number and placement of the attachment members 18 may be modified in the computer code that runs the program of the CNC machine. A computer operated laser-cutting machine may also produce precise analogous surface structures in the device using photon energy or ablation instead of mechanical cutting.

According to various embodiments of the subject disclosure, mold-making begins with melting paraffin wax into a petri dish, and covering it to let the wax cool slowly and evenly. In some embodiments, the tips of No. 11 surgical blades may be used to penetrate the wax at a desired depth (e.g., at about 2 millimeters) and at a desired angle (e.g., at about 20 degrees) from the surface, leaving negatives of what will become the attachment members 18. The casting polyurethane, for example, Alumilite, may be cast onto the wax mold and placed in a vacuum (e.g., at −22 mmHg) to ensure all the gas from the small negative spaces are evacuated out so as to produce a precise positive of the entire array of attachment members 18. Following curing and removal from the wax mold, the Alumilite positive may be placed in another petri dish, with the attachment members 18 side facing up, where a room temperature curing platinum silicone elastomer, for example VST-50 from Factor II, Inc., can be cast over the Alumilite and placed in vacuum to ensure complete fidelity to the Alumilite positive. After curing, the silicone elastomer can be peeled off the Alumilite and used as the final heat-resistant, reusable master mold.

In some embodiments, fabrication of the fixation device 10 may involve a two-part technique to create a bimodal, composite material with rigid attachment members 18 and the carrier member 12 (e.g., an elastomeric film). To create the attachment members 18 for the carrier member 12, a rigid material is cast into the mold to provide the strength needed to support resisting forces. In some embodiments, the attachment members 18 comprise a polymer. In some embodiments, the attachment members 18 comprise at least one of a thermoplastic (e.g., poly(methyl methacrylate) (PMMA), PMMA-copolymers, and Acrylotem-M from Ovation Polymers), ultraviolet curable resin (e.g., UV-Cure 7165 from Deco-Coat Products), biodegradable polyester (e.g., polycaprolactone from Sigma-Aldrich and poly(L-lactide) from Sigma-Aldrich), biomedical grade polycarbonate urethane (e.g., Bionate 75D from DSM Biomedical), shape memory polyesters and polyurethanes (e.g., from DSM Biomedical), and degradable polyurethane. These materials may be medical grade. The biodegradable polyester may comprise at least one of polycaprolactone, poly(L-lactide), poly(D,L-lactide), and poly(glycolide-co-lactide), wherein the molecular weight of the polycaprolactone is between about 150,000 and 250,000 and the molecular weight of the poly(L-lactide), poly(D,L-lactide), or poly(glycolide-co-lactide) is between about 150,000 and 250,000. In some embodiments, the molecular weight of the polycaprolactone may be less than about 150,000 and the molecular weight of the poly(L-lactide), poly(D,L-lactide), or poly(glycolide-co-lactide) may be less than about 150,000. In some embodiments, the molecular weight of the polycaprolactone may be greater than about 250,000 and the molecular weight of the poly(L-lactide), poly(D,L-lactide), or poly(glycolide-co-lactide) may be greater than about 250,000. In some embodiments, the attachment member 18 comprises non-polymeric resorbable biomaterials including calcium-based ceramics (e.g., calcium phosphates, various hydroxyapatites, carbonates or sulfates), biocompatible silicates (e.g., bioglasses), silicon or titanium nitrides or oxides, or their composites with degradable polymers (e.g., biomedical grade degradable or non-degradable polyester or polyurethane).

In some embodiments, the carrier member 12 comprises an elastomer, preferably a medical grade elastomer. In some embodiments, the carrier member 12 comprises a degradable medical grade elastomer. In some embodiments, the carrier member 12 comprises a shape memory degradable elastomer (e.g., segmented polyester urethane). In some embodiments, the carrier member 12 comprises a shape memory non-degrading elastomer. In some embodiments, the carrier member 12 comprises at least one of an ultraviolet curable resin (e.g., Acrylotem-P-Soft-85 from Ovation polymers), methacrylated polybutadiene (e.g., Ricacryl 3500 from Sartomer), and polyether urethane (e.g., Biospan Segmented Polyether Urethane from DSM Biomedical).

In some embodiments, for a thermal melt, the attachment members 18 may comprise at least one of polycarbonate urethane (e.g., Bionate 75D from DSM Biomedical), polycaprolactone, poly(L-lactide), poly(D,L-lactide), and poly(glycolide-co-lactide), wherein the molecular weight of the polycaprolactone is between about 150,000 and 250,000 and the molecular weight of the poly(L-lactide), poly(D,L-lactide), or poly(glycolide-co-lactide) is between about 150,000 and 250,000. In some embodiments, for a thermal melt, the carrier member 12 may comprise polyether urethane (e.g., Biospan Segmented Polyether Urethane from DSM Biomedical). For a thermal melt, the polymer pellets are placed over the silicone mold in a vacuum oven and heated to melting point under vacuum. As the polymer melts, the polymer may flow into the spaces in the mold as the atmospheric gas is evacuated out. While the polymer is still in a liquid phase, the excess can be removed (e.g., by using a drawing blade or straight-edge razor blade as a squeegee), leaving behind the polymer only in the attachment member 18 cavities where the polymer can solidify again.

In some embodiments, for an ultraviolet (UV) photo-crosslinking cure, the attachment members 18 may comprise at least one of a thermoplastic (e.g., poly(methyl methacrylate) (PMMA), PMMA-copolymers, and Acrylotem-M from Ovation Polymers) and ultraviolet curable resin (e.g., UV-Cure 7165 from Deco-Coat Products) or photo-curable polymer resin. These materials may be medical grade. In some embodiments, for a UV cure, the carrier member 12 may comprise at least one of ultraviolet curable resin (e.g., Acrylotem-P-Soft-85 from Ovation Polymers) and methacrylated polybutadiene (e.g., Ricacryl 3500 from Sartomer) or photo-curable polymer resin. To use a UV curable technique, the UV curable polymer or its solutions can be poured over the silicone molds and then placed in vacuum to remove ambient atmosphere and completely fill the small spaces in the mold. After vacuum, the excess will be removed (e.g., by using a drawing blade or straight-edge razor blade as a squeegee), and then the remaining polymer can be exposed UV light (wavelength .about.360-365 nm, 10 mW/cm2) for approximately 1 minute to cure the resin in situ. The bulk portion of the fixation device 10 may created by casting an elastomeric polymer directly over the attachment members 18 still within the mold and curing or cooling to ambient temperature.

Using a thermal melt process, the carrier polymer can be heated to melting point and then simply cast onto the mold over the attachment members 18. Similarly, a UV curable polymer solution can be cast over the attachment members 18 and then exposed to UV light to cure. After the elastomeric portion has cooled, the carrier member 12 can be pulled off the silicone mold with the attachment members 18 intact within the carrier film, and exposed and decorated on and across its surface. In some embodiments, fabrication based on the foregoing techniques may reduce manufacture time and enhance device dimensional precision and fidelity and resulting physical feature qualities without the need of solvent chemistry.

In some embodiments, the fixation device 10 may be loaded at various mass fractions (doses) with bioactive or pharmacologically active or included biodegradable materials that release bioactive molecules, such as drugs (e.g., antibiotics, anti-inflammatories, anti-thrombotics, anti-fibrotics) and growth factors known to promote tissue repair. For example, antibiotics may include ceftazidime, gentamicin, tobramycin, vancomycin, and/or other suitable antiobiotics. Anti-thrombotics may include warfarin, heparins, and/or other suitable anti-thrombotics. The bioactive inclusions can be loaded directly into any carrier member 12 or attachment member 18 materials for controlled release to the tissue surface over time without degradable materials. They can also be included deliberately within biodegradable carrier member 12 or attachment member 18 materials, or in biodegradable matrices within such materials (for example as micro- or nano-encapsulated drugs). For example, at least one of the carrier member 12 and the attachment members 18 may comprise biodegradable materials capable of holding and then releasing drugs upon degradation. The biodegradable material may include biodegradable polyester or biodegradable polyurethanes. In some embodiments, the biodegradable polyester comprises at least one of polycaprolactone, poly(L-lactide), poly(D,L-lactide), and poly(glycolide-co-lactide), wherein the molecular weight of the polycaprolactone is between about 150,000 and 250,000 and the molecular weight of the poly(L-lactide), poly(D,L-lactide), or poly(glycolide-co-lactide) is between about 150,000 and 250,000. In some embodiments, the molecular weight of the polycaprolactone may be less than about 150,000 and the molecular weight of the poly(L-lactide), poly(D,L-lactide), or poly(glycolide-co-lactide) may be less than about 150,000. In some embodiments, the molecular weight of the polycaprolactone may be greater than about 250,000 and the molecular weight of the poly(L-lactide), poly(D,L-lactide), or poly(glycolide-co-lactide) may be greater than about 250,000. In some embodiments, at least one of (a) the carrier member 12 and (b) the attachment members 18 comprises a connective tissue growth factor. The connective tissue growth factor can be part of the CCN family (e.g., CCN2) or comprise other suitable pharmacologically active factors known to those of ordinary skill in the art. In some embodiments, when a part 14 is attached to a portion 40 of connective tissue and as the biodegradable material progressively biodegrades, the connective tissue growth factor may be progressively released for promoting repair of the portion 40 of connective tissue. In some embodiments, at least part of the carrier member 12 may be permeable (e.g., for facilitating molecule diffusion into and/or out of portions 40 of connective tissue).

In some embodiments, anti-adhesive, anti-fibrotic, anti-inflammatory, and/or hydrophilic lubricious materials may be incorporated on the opposing surface 20 of the fixation device to prevent non-desirable adhesion formations. For example, the carrier member 12 may comprise a surface (e.g., opposing surface 20 and/or tissue-facing surface 22) having at least one of an anti-inflammatory material (e.g., corticosteroid, other suitable steroids, or other suitable anti-fibrotic materials known to those of ordinary skill in the art), an anti-thrombotic material, and an anti-biotic material, within, released from or on the carrier member 12. In some embodiments, these bioactive materials or other suitable biomaterials (e.g., slippery, wettable lubricious coatings based on hydrophilic polymers) known to those of ordinary skill in the art may be used to reduce adhesion formations on the surface. In some embodiments, at least part of the carrier member 12 is hydrophilic, wetting and lubricious against tissue surfaces. In some embodiments, at least part of the carrier member 12 comprises a swellable material. The swellable material may comprise a hydrogel. In some embodiments, at least one of the carrier member 12 and the attachment member 18 comprises a shape memory material.

According to various embodiments of the subject disclosure, each attachment member 18 extending from the carrier member 12 may be coupled to the carrier member 12 using a stabilizing member that is configured to resist angular motion of a respective attachment member 18 relative to the carrier member 12. This provides stability for each attachment member 18 so that each attachment member 18 may remain substantially positionally fixed relative to the carrier member 12. In some embodiments, the stabilizing member allows for greater working strength for a respective attachment member 18 and improves angular stability of the respective attachment member 18 relative to the carrier member 12. In some embodiments, stabilizing members are provided to allow for consistent attachment of each attachment member 18 to the carrier member 12.

FIGS. 14A, 14B, 14C, 14D, 14E, 14F, 14G, and 14H illustrate examples of an attachment member 18 coupled to a stabilizing member 62, in accordance with various embodiments of the subject disclosure. The stabilizing member 62 is configured to couple attachment member 18 to the carrier member 12, and is substantially positionally fixed relative to the carrier member 12. In some embodiments, the stabilizing member 62 is configured to resist angular motion of the attachment member 18 relative to the carrier member 12.

According to certain embodiments, the stabilizing member 62 resides at least partially in the carrier member 12. For example, the stabilizing member 62 may reside fully within the carrier member 12. In some embodiments, the stabilizing member 62 may be coupled to an outer surface of the carrier member 12. In some embodiments, the stabilizing member 62 is substantially parallel to a face of the carrier member 12. In some embodiments, the stabilizing member 62 is substantially perpendicular to the attachment member 18.

According to certain embodiments, the stabilizing member 62 may be integral with the attachment member 18. In some embodiments, the stabilizing member 62 forms a base of the attachment member 18. In some embodiments, a length of the stabilizing member 62 is greater than or equal to a height of the attachment member 18. The attachment member 18 is configured to penetrate at least partially the connective tissue. In some embodiments, the attachment member 18 extends substantially perpendicular from the stabilizing member 62. When fixation device 10, for example, is being affixed to connective tissue, the stabilizing member 62 can resist angular motion of the attachment member 18 during the affixing. Thus, bending of the attachment member 18 relative to the carrier member 12 can be minimized.

Figure 15A:
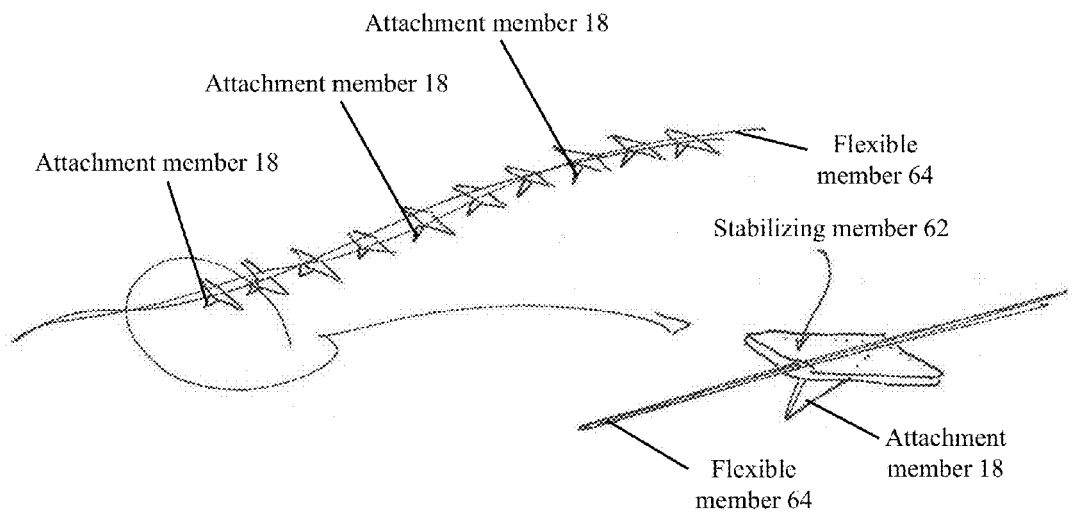
FIGS. 15A and 15B illustrate an example of a flexible member used to connect one or more attachment members, in accordance with various embodiments of the subject disclosure.
Figure 15B:
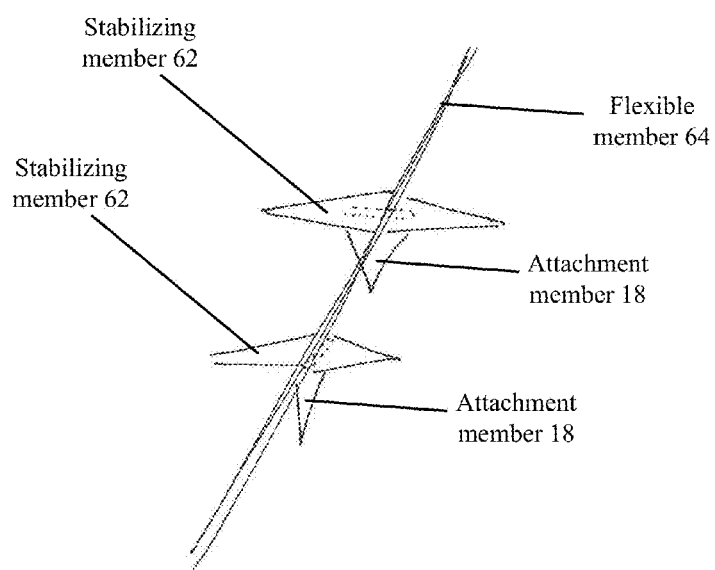

According to certain embodiments, a flexible member can be cast as a rigid interconnection between the attachment members 18. FIGS. 15A and 15B illustrate an example of a flexible member 64 used to connect one or more attachment members 18, in accordance with various embodiments of the subject disclosure. As shown in these figures, flexible member 64 connects a plurality of attachment members 18. The flexible member 64 can comprise at least one of a fiber, a filament, a string, a thread, and a line. In some embodiments, the flexible member 64 can be made of at least one of polyethelene, poly glycolic acid, and nylon. According to certain embodiments, the flexible member 64 can reside at least partially in the carrier member 12. For example, the first flexible member may be embedded in the carrier member 12. In some embodiments, the flexible member 64 resides at least partially in the stabilizing member 62 of an attachment member 18. The flexible member 64 may allow for anisometric behavior of the carrier member 12.

Figure 16A:
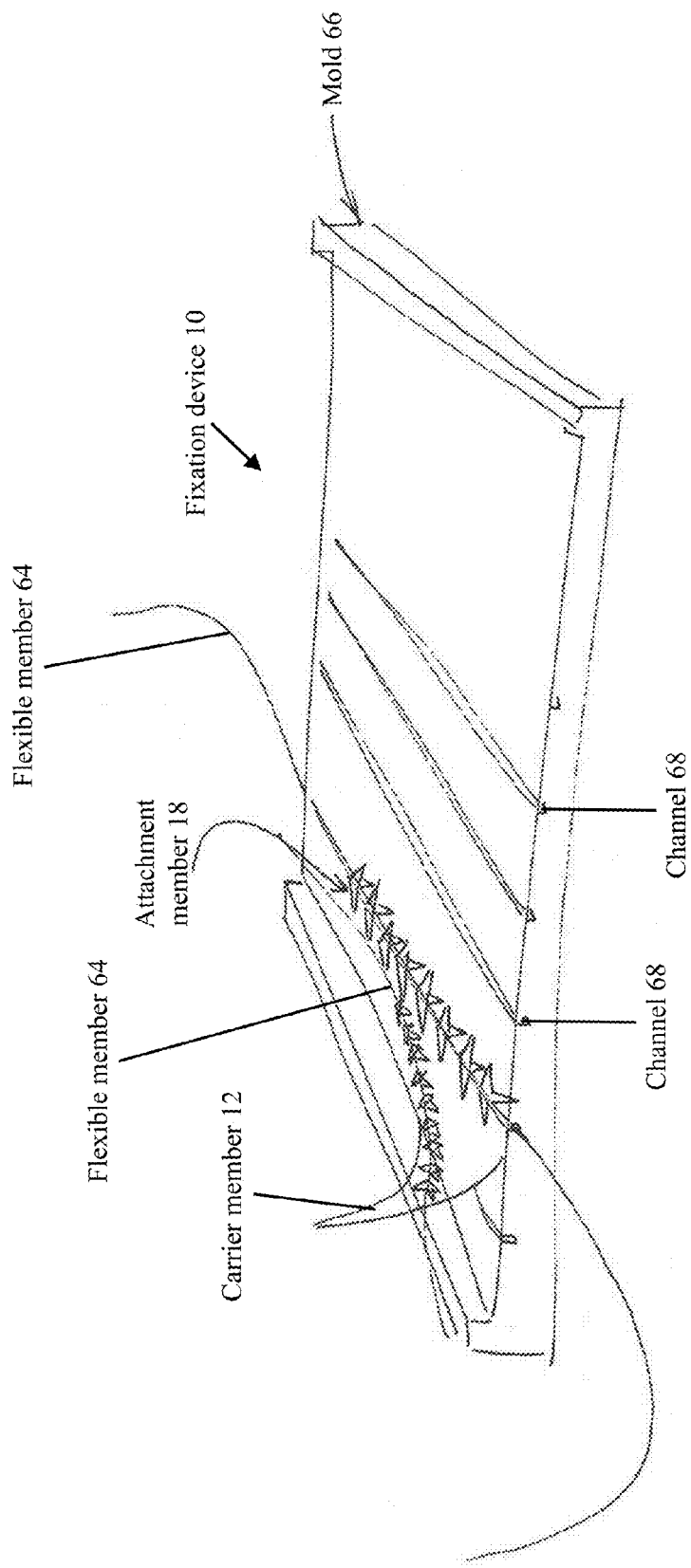
FIG. 16A illustrates an example of fabricating a fixation device, in accordance with various embodiments of the subject disclosure.

As shown in FIG. 16A, flexible members 64 may be used to facilitate removal of an attachment member 18 and the carrier member 12 from a mold 66 used to fabricate the fixation device 10. Each flexible member 64 may be placed within a channel 68 of mold 66, wherein each channel 68 interconnects the negatives for the attachment members 18. In some embodiments, the attachment members 18 may be cast as repeating units. For example, rigid polymer may be molded in repeating unit wells within mold 66 to form the attachment members 18. In some embodiments, material for the carrier member 12 (e.g., elastomer) may be laid as a film within mold 66. For example, the elastomer is cast as a layer which binds the attachment members 18 and the flexible members 64 into a single construct to form the fixation device 10.

The flexible members 64 may be configured in different arrangements relative to one another. Thus, the attachment members 18 that are interconnected by the flexible members 64 may be configured in different arrangements as well. For example, a first flexible member 64 may connect a first set of attachment members 18 (e.g., forming a row of attachment members 18). A second flexible member 64 may connect a second set of attachment members 18 (e.g., forming another row of attachment members 18). In some embodiments, the first set of attachment members 18 may be aligned with the second set of attachment members 18 such that a long axis of the first set of attachment members 18 is substantially parallel to a long axis of the second set of attachment members 18.

According to various embodiments of the subject technology, the flexible members 64 can be used to prevent the attachment members 18 from substantially cutting and/or applying substantial stress to the connective tissue during physiological use of the connective tissue. For example, when the attachment members 18 are engaged with the connective tissue, the connective tissue may stretch or contract during physiological use of the connective tissue. If the carrier member 12 does not stretch or contract in substantially the same manner as the connective tissue, the attachment members 18 may remain fixed relative to the connective tissue, thereby cutting and/or applying substantial stress to the connective tissue. According to various embodiments of the subject technology, an elasticity of at least one of a flexible member 64 and the carrier member 12 is substantially the same as an elasticity of the connective tissue. Thus, the carrier member 12 and/or a flexible member 64 (which may connect a set of attachment members 18), may stretch or contract in substantially the same manner as the connective tissue during physiological use of the connective tissue and prevent the attachment members 18 from cutting and/or applying substantial stress to the connective tissue. In some embodiments, an elasticity of at least one of a flexible member 64 and the carrier member 12 is slightly greater than an elasticity of the connective tissue. This may allow the flexible member 64 and/or the carrier member 12 to sufficiently hold the connective tissue in place depending on the application of the flexible member 64 and/or the carrier member 12.

According to certain embodiments, the flexible member 64 may comprise one or more adjustment members configured to resize a length of the flexible member 64. In this way, the flexible member 64 may stretch or contract in substantially the same manner as the connective tissue. For example, the one or more adjustment members may be configured to resize the length of the flexible member 64 such that the length of the flexible member 64 is substantially the same as a length of the connective tissue (e.g., engaged by the attachment members 18) during physiological use of the connective tissue. In some embodiments, each adjustment member comprises at least one of a coil, a curve, a kink, and some other suitable structure for resizing the length of the flexible member 64 to match the length of the connective tissue. In some embodiments, each adjustment member may act like a spring (e.g., for stretching or contracting a corresponding flexible member 64). FIGS. 16B and 16C illustrate examples of an adjustment member 102, in accordance with various embodiments of the subject technology.

Figure 17A:
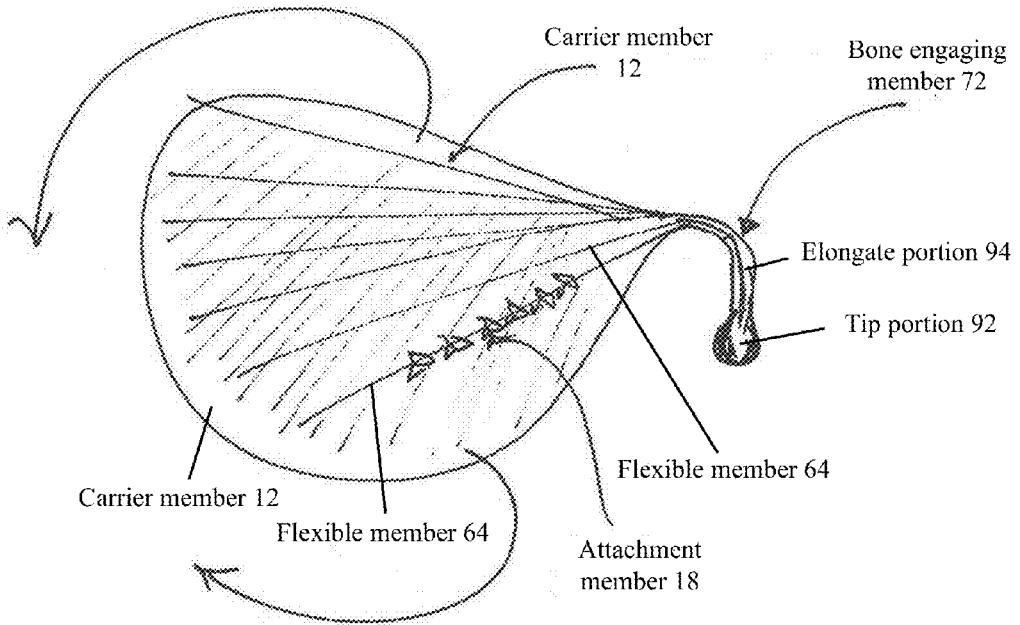
FIG. 17A illustrates an example of a fixation device for fixating connective tissue to bone, in accordance with various embodiments of the subject disclosure.

According to various embodiments of the subject technology, the carrier member 12 as described herein may be used in conjunction with a bone engaging member 72 to facilitate soft tissue fixation to bone. FIG. 17A illustrates an example of a fixation device 100 for fixating connective tissue to bone, in accordance with various embodiments of the subject disclosure. The fixation device 100 comprises the carrier member 12. The fixation device 100 also comprises the plurality of attachment members 18 extending from the carrier member 12 and configured to engage connective tissue of an animal. The fixation device 100 also comprises the bone engaging member 72 extending from the carrier member 12 and configured to attach to a bone of the animal. In some embodiments, when the plurality of attachment members 18 is engaged with the connective tissue and the bone engaging member 72 is attached to the bone, the connective tissue and the bone are limited in being pulled apart from one another during physiological use of the connective tissue.

In some embodiments, the carrier member 12 and the bone engaging member 72 are integral with one another. The carrier member 12 comprises a sheet, and is configured to conform to the connective tissue. For example, the carrier member 12 may wrap around the connective tissue. The carrier member 12 can comprise various suitable shapes. For example, the carrier member 12 comprises at least one of a leaf shape, a tear drop shape, and a fusiform shape.

According to certain embodiments, flexible members 64 may be used to connect rows of attachment members 18 on carrier member 12. The flexible members 64 may fan out in a direction away from the bone engaging member 72. In some embodiments, the bone engaging member 72 may comprise the flexible members 64 being brought together from the carrier member 12 to form a stem-like structure that may be pre-loaded into an aperture within the bone.

Figure 17B:
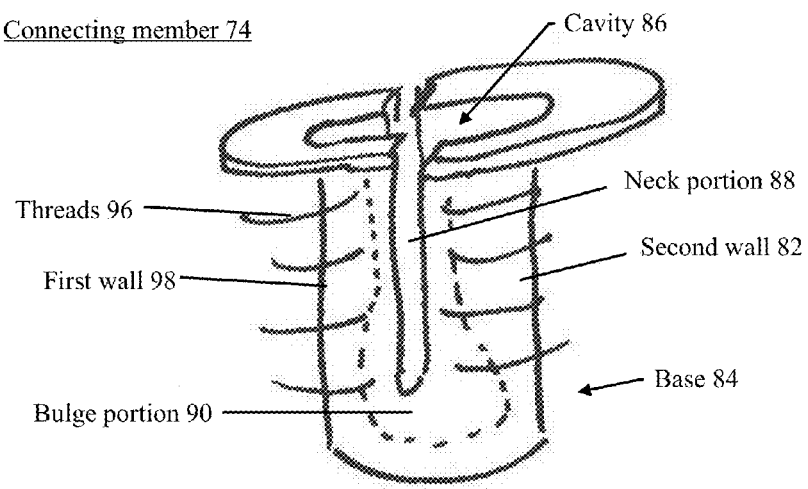
FIG. 17B illustrates an example of a connecting member, in accordance with various embodiments of the subject disclosure.

FIG. 17B illustrates an example of a connecting member 74, in accordance with various embodiments of the subject disclosure. The connecting member 74 may be inserted into the aperture within the bone and is used to facilitate the attachment of the bone engaging member 72 to the bone.

FIG. 18A illustrates an example of connective tissue 76 and a bone 78 prior to being fixated to one another, in accordance with various embodiments of the subject disclosure. The connective tissue 76 comprises at least one of a ligament and a tendon. FIG. 18B illustrates an example of the connective tissue 76 and the bone 78 being fixated to one another using the fixation device 100, in accordance with various embodiments of the subject disclosure.

Referring to FIGS. 17A, 17B, 18A and 18B, the bone engaging member 72 is configured to be inserted into an aperture 80 within the bone 78. In some embodiments, the connecting member 74 is configured to be inserted into the aperture 80, and the bone engaging member 72 is attached to the bone 78 by being inserted into the connecting member 74 when the connecting member 74 is inserted into the aperture 80 within the bone 78.

According to certain embodiments, the connecting member 74 comprises a first wall 98, a second wall 82 attached to the first wall 98 at a base 84 of the connecting member 74, and a cavity 86 therebetween. The connecting member 74 is configured such that the first wall 98 and the second wall 82 is displaceable relative to one another. At least one of the first wall 98 and the second wall 82 is configured to be displaced relative to the base 84 of the connecting member 74. In some aspects, an outer surface of the first wall 98 and/or the second wall 82 comprises a plurality of threads 96 configured to engage an inner surface of the aperture 80 within the bone 78. Thus, the connecting member 74 may be screwed into the bone 78.

In some embodiments, the cavity 86 comprises a neck portion 88 and a bulge portion 90. The bulge portion 90 is positioned at the base of the connecting member 74. In some embodiments, the bulge portion 90 has a larger volume than the neck portion 88 when the first wall 98 and the second wall 82 are not displaced relative to one another. The bone engaging member 72 comprises a tip portion 92 sized to fit within the bulge portion 90 of the cavity 86. For example, the tip portion 92 may comprise a fusiform shape that allows it to be interlocked within the bulge portion 90. The bone engaging member 72 comprises an elongate portion 94 sized to fit within the neck portion 88 when the first wall 98 and the second wall 82 are not displaced relative to one another.

According to certain embodiments, to insert the bone engaging member 72 into the connecting member 74, the first wall 97 and the second wall 82 may be displaced relative to one another from a first position to a second position. The bone engaging member 72 may be inserted into the aperture 80 such that the tip portion 92 fits within the bulge portion 90. Then the first wall 97 and the second wall 82 may then be permitted to return toward the first position such that the elongate portion 94 fits within the neck portion 88 of the cavity 86.

According to various embodiments of the subject disclosure, the hoop stresses imparted to a tendon by the fixation device as described herein (e.g., fixation device 10 or fixation device 100) may maintain intratendinous pressure less than the mean arterial pressure to prevent local ischemia within the fixated tendon (e.g., absolute value is less than about 45 mmhg). In some embodiments, the fixation device as described herein may be used for various applications, including but not limited to, augmentation abdominal wound closure, hernia repair, and veterinary applications.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. An apparatus, for fixating connective tissue to bone, comprising:
   a carrier member having a length, width, and thickness, the length and width each being at least two times greater than the thickness, the carrier member including a flexible member such that the flexible member includes an adjustment portion;
   a plurality of attachment members extending from the carrier member and configured to engage connective tissue of an animal, the plurality of attachment members extending from and along the flexible member of the carrier member; and
   a bone engaging member extending from the carrier member and configured to attach to a bone of the animal;
   wherein, upon the plurality of attachment members being engaged with the connective tissue and the bone engaging member being attached to the bone, the adjustment portion of the flexible member is configured to lengthen or shorten a spacing between the attachment members engaging the connective tissue along the flexible member as the connective tissue respectively stretches or contracts during physiological use of the connective tissue.

2. The apparatus of claim 1, wherein the carrier member and the bone engaging member are integral relative to one another.

3. The apparatus of claim 1, further comprising a connecting member configured to be inserted into an aperture within the bone, wherein the bone engaging member is attached to the bone by being inserted into the connecting member when the connecting member is inserted into the aperture within the bone.

4. The apparatus of claim 3, wherein the connecting member comprises a first wall, a second wall attached to the first wall at a base of the connecting member, and a cavity therebetween, the connecting member configured such that the first wall and the second wall is displaceable relative to one another.

5. The apparatus of claim 4, wherein at least one of the first wall and the second wall is configured to be displaced relative to the base of the connecting member.

6. The apparatus of claim 4, wherein the cavity comprises a neck portion and a bulge portion, the bulge portion positioned at the base of the connecting member, the bulge portion having a larger volume than the neck portion when the first wall and the second wall are not displaced relative to one another.

7. The apparatus of claim 6, wherein the bone engaging member comprises a tip portion sized to fit within the bulge portion of the cavity of the connecting member.

8. The apparatus of claim 6, wherein the bone engaging member comprises an elongate portion sized to fit within the neck portion of the cavity when the first wall and the second wall are not displaced relative to one another.

9. The apparatus of claim 4, wherein an outer surface of the first wall comprises a plurality of threads configured to engage an inner surface of the aperture within the bone.

10. The apparatus of claim 1, further comprising a plurality of stabilizing members each configured to couple a respective attachment member to the carrier member, each stabilizing member being substantially positionally fixed relative to the carrier member.

11. The apparatus of claim 1, further comprising a first flexible member connecting a first set of the plurality of attachment members.

12. The apparatus of claim 11, further comprising a second flexible member connecting a second set of the plurality of attachment members.

13. The apparatus of claim 12, wherein the first set of the plurality of attachment members is aligned with the second set of the plurality of attachment members such that a distance between the first flexible member and the second flexible member is greater at a first half of the carrier member than at a second half of the carrier member, the second half positioned between the first half and the bone engaging member.

14. The apparatus of claim 1, wherein the carrier member comprises at least one of a polymeric material and a metallic material.

15. An apparatus, for fixating connective tissue to bone, comprising:
a carrier member having a length, width, and thickness, the length and width each being at least two times greater than the thickness, the carrier member including a bone engaging portion extending from the carrier member such that the bone engaging portion is configured to be coupled to the bone, the carrier member including a flexible portion with attachment portions extending from and along the flexible portion, the attachment portions extending from the carrier member and configured to engage the connective tissue, the flexible portion having an adjustment portion;
wherein, upon the attachment portions being engaged with the connective tissue and the bone engaging portion being attached to the bone, the adjustment portion of the flexible portion is configured to lengthen or shorten a spacing between the attachment portions engaging the connective tissue along the flexible portion as the connective tissue respectively stretches or contracts during physiological use of the connective tissue.

16. The apparatus of claim 15, wherein the carrier member is integral to the bone engaging portion.

17. The apparatus of claim 15, wherein the carrier member comprises a sheet structure.

18. The apparatus of claim 15, wherein the flexible portion comprises multiple filaments extending along the carrier member.

19. The apparatus of claim 15, wherein the adjustment portion of the flexible portion comprises at least one of a coil structure, a curved structure, and a kinked structure.

20. The apparatus of claim 15, wherein the carrier member comprises at least one of a polymeric material and a metallic material.

* * * * *